(12) United States Patent
Kim

(10) Patent No.: US 10,069,070 B2
(45) Date of Patent: Sep. 4, 2018

(54) METHOD AND APPARATUS FOR PURIFYING ORGANIC MATERIAL BY USING IONIC LIQUID

(71) Applicant: ILSOLED CO., LTD., Buk-gu, Gwangju (KR)

(72) Inventor: Tae Won Kim, Gwangju (KR)

(73) Assignee: ILSOLED CO., LTD., Buk-gu, Gwangju (KR)

( * ) Notice: Subject to any disclaimer, the term of this patent is extended or adjusted under 35 U.S.C. 154(b) by 0 days.

(21) Appl. No.: 15/118,288

(22) PCT Filed: Feb. 11, 2015

(86) PCT No.: PCT/KR2015/001378
§ 371 (c)(1),
(2) Date: Aug. 11, 2016

(87) PCT Pub. No.: WO2015/122686
PCT Pub. Date: Aug. 20, 2015

(65) Prior Publication Data
US 2016/0372673 A1    Dec. 22, 2016

(30) Foreign Application Priority Data

Feb. 14, 2014    (KR) .................. 10-2014-0017496
Feb. 14, 2014    (KR) .................. 10-2014-0017506
(Continued)

(51) Int. Cl.
*H01L 51/00*    (2006.01)
*H01L 51/56*    (2006.01)
(Continued)

(52) U.S. Cl.
CPC ............ *H01L 51/0025* (2013.01); *B01D 7/00* (2013.01); *B01D 9/005* (2013.01); *C07C 209/84* (2013.01);
(Continued)

(58) Field of Classification Search
None
See application file for complete search history.

(56) References Cited

U.S. PATENT DOCUMENTS

2016/0193543 A1*    7/2016    Kim .................. B01D 7/02
564/308

FOREIGN PATENT DOCUMENTS

JP    2004018468 A    1/2004
JP    2006075740 A    3/2006
(Continued)

OTHER PUBLICATIONS

Int'l Search Report dated May 20, 2015 in Int'l Application No. PCT/KR2015/001378.

*Primary Examiner* — Clinton A Brooks
(74) *Attorney, Agent, or Firm* — Panitch Schwarze Belisario & Nadel LLP

(57) ABSTRACT

A method of purifying an organic material using an ionic liquid according to the present invention includes a sublimation step (S510) of sublimating the organic material containing an impurity, a capturing step (S520) of bringing a sublimated gas of the organic material into contact with the flowing ionic liquid to capture the sublimated gas, and a recrystallization step (S530) of preferentially oversaturating the organic material, which is to be purified, of the sublimated gas, which is captured in the ionic liquid to be dissolved, to thus generate the recrystallized organic material. In the present invention, it is not necessary to perform a process of carrying the sublimated gas, which is generated (Continued)

during the sublimation step, to implement reverse sublimation. Accordingly, there is a merit in that the contamination of a purified sample by an inert carrier gas, which is used in a conventional sublimation purification method, is fundamentally avoided.

20 Claims, 20 Drawing Sheets

(30) Foreign Application Priority Data

| Feb. 24, 2014 | (KR) | 10-2014-0021550 |
| Feb. 24, 2014 | (KR) | 10-2014-0021551 |
| Mar. 18, 2014 | (KR) | 10-2014-0031872 |
| May 13, 2014 | (KR) | 10-2014-0057339 |
| Jan. 27, 2015 | (KR) | 10-2015-0012661 |

(51) Int. Cl.
*B01D 7/00* (2006.01)
*B01D 9/00* (2006.01)
*C07C 209/84* (2006.01)
*C07C 211/54* (2006.01)
*H01L 51/50* (2006.01)

(52) U.S. Cl.
CPC ............ *C07C 211/54* (2013.01); *H01L 51/56* (2013.01); *B01D 2009/0086* (2013.01); *H01L 51/006* (2013.01); *H01L 51/0058* (2013.01); *H01L 51/5056* (2013.01)

(56) References Cited

FOREIGN PATENT DOCUMENTS

| JP | 2013116879 A | 6/2013 | |
| JP | 2013209352 A | 10/2013 | |
| KR | 20040104832 A | 12/2004 | |
| KR | 20120121269 A | 11/2012 | |
| WO | WO2014098458 * | 6/2014 | ............ C07B 63/00 |

* cited by examiner

METHOD AND APPARATUS FOR PURIFYING ORGANIC MATERIAL BY USING IONIC LIQUID

CROSS-REFERENCE TO RELATED APPLICATION

This application is a Section 371 of International Application No. PCT/KR2015/001378, filed Feb. 11, 2015, which was published in the Korean language on Aug. 20, 2015, under International Publication No. WO 2015/122686 A1, and the disclosure of which is incorporated herein by reference.

TECHNICAL FIELD

The present invention relates, in general, to a method and an apparatus for purifying an organic material using an ionic liquid and, more particularly, to a method and an apparatus for purifying an organic material using an ionic liquid to thus obtain a highly pure low-molecular weight organic material, which is usable as a luminous body or a transporter of an organic EL (electroluminescence) device. Further, the present invention relates to an organic material purified using the purification method.

BACKGROUND ART

An organic EL device includes a transparent anode, which has a large work function, a cathode metal, which has a small work function, and a plurality of organic thin film layers therebetween. The organic EL device is a display based on a light-emitting principle whereby, when a voltage is applied to the device in a forward direction, holes are injected from the anode to an organic layer, electrons are injected from the cathode, and recombination occurs in a light-emitting layer to thus emit light. The organic EL has high-quality panel characteristics, such as low power consumption, a wide viewing angle, a fast response speed, and a wide driving temperature range, which are required in the information age. Further, the organic EL has a merit in that costs are low compared to conventional flat panel displays, attributable to the relatively simple manufacturing process.

The purity of the organic material is a factor affecting the light emission properties of the organic EL device. When impurities are mixed with organic materials, the impurities serve as traps of carriers or cause the extinction of light to thus reduce the intensity of emitted light and the light emission efficiency. Therefore, there is a need to purify the organic materials in order to remove the impurities.

The organic material generally undergoes a purification process using a chemical method after synthesis. Examples of the chemical purification process may include recrystallization, distillation, and column chromatography. The purity of the target compound may be increased to 99% or more using the chemical purification process.

Typical examples of the purification process of the organic material include recrystallization using a solvent or recrystallization by sublimation. Recrystallization using the solvent has a merit of bulk purification of the organic material, but a drawback in that the use of the solvent means that the solvent easily penetrates organic crystals. That is, the solvent, which penetrates the organic crystals, serves as an impurity to thus reduce the light emission properties.

Other examples of the purification process include a chromatography process such as high-performance liquid chromatography (HPLC). When such a chromatography process is used to perform purification, the purity may be higher than that achieved via simple chemical purification process. However, generally, the chromatography process is only used for the purpose of analysis and is considered as a process which is unsuitable for purification of the material during mass production.

An organic light-emitting material is typically purified using a sublimation purification process. Sublimation refers to a transition phenomenon between solid and gas phases at a temperature and pressure below a triple point in a phase equilibrium diagram. Thermally decomposed by heat at normal pressure, the material is not decomposed even at a relatively high temperature under the low pressure below the triple point. The process of heating a synthesized material to separate the material from an impurity, which has a sublimation point different from that of the material, using the aforementioned characteristic without decomposing the material in a sublimation apparatus having a controllable temperature gradient is referred to as a vacuum sublimation process. The vacuum sublimation process is a purely physical process and does not rely on the use of auxiliary reagents or other chemical processes. Therefore, the vacuum sublimation process has a merit in that high-purity purification is feasible because samples are not contaminated, and accordingly, the vacuum sublimation process is known as a process that is useful for purifying an organic material for organic EL devices.

Currently, the most extensively used ultra-high-purity purification process of the organic material is a vacuum train sublimation purification process. In this process, a long tube-type chamber in a near-vacuum state is divided into a plurality of heating zones, and the materials are heated in the heating zones at different temperatures, which range from a high temperature to a low temperature, to thus ensure a temperature gradient across the materials. In the process, only the material that is deposited in a specific heating zone is used by taking advantage of the differences between the sublimation points of the materials sublimated in the chambers.

Typically, a conventional vacuum sublimation purification process is performed under the following process conditions.

(1) The heating zone is divided into three to nine zones. When the number of divided zones is small, high, intermediate, and low temperature types are used. When the number of divided zones is large, heating temperatures are set within a temperature gradient range including the zones from which the samples are taken and other zones.

(2) The sample loading zone is situated at the position opposite the vacuum pump.

(3) Although there is variation due to the properties of the materials, the initial pressure of the chamber is in the range of $10^{-2}$ to $10^{-6}$ torr before a carrier gas flows, and the pressure of the side on which the carrier gas flows is controlled to be maintained at 0.1 to several torr. Highly pure nitrogen or argon gas having no reactivity is used as the carrier gas.

(4) The loading of the sample is set so that the loading volume of the sample does not exceed ½ of the diameter of the tube if possible, in order to cause the carrier gas to move through the tube. A boat-shaped loading tool may be used.

The purpose of using the carrier gas in the conventional vacuum sublimation purification process is to improve the flowability of the sample in a vacuum sublimation state. That is, when the carrier gas is not present in a state close to a vacuum, the flowability of the sublimated sample molecules is poor, and thus solid particles are deposited on the wall of the zone, which is very close to the sample loading zone. Therefore, a basic process condition includes the use of the carrier gas in the conventional vacuum sublimation purification process.

However, the conventional vacuum sublimation purification process has some drawbacks. The biggest problem with the conventional vacuum sublimation purification process is that a predetermined zone, including an ultra-high purity material formed therein, is contaminated by the carrier gas. That is, the original samples, loaded in the sample loading zone, are scattered by the carrier gas to thus contaminate the zone including the ultra-high purity material deposited therein. Further, the carrier gas gradually transports the zone, including the ultra-high purity material deposited therein, to a third zone.

The carrier gas not only plays the aforementioned adverse role during the process, but it also strains the apparatus when the sample is loaded in a large amount. Accordingly, a portion of the sublimated sample contaminates a vacuum pump. Although a trap apparatus having a high-capacity structure is provided in order to prevent such contamination, the performance of the vacuum pump is still reduced.

Another drawback with the conventional vacuum sublimation purification process is scattering during vacuum venting. Nitrogen gas is supplied into the chamber to create normal pressure during vacuum venting. In this case, the samples, which undergo the purification process, may be scattered in the chamber. When both ends of the glass tube for purification (or quartz tube) are opened, the scattering is further aggravated, thus frequently contaminating materials that have been purified in advance.

In short, the sublimation purification process has a merit in that the raw materials are purified into the highly pure organic material using the differences between the sublimation points of the organic materials, but has various problems as follows.

(1) Since a significant amount of the organic material is exhausted to the atmosphere together with the carrier gas while sublimation and reverse sublimation are repeated during the purification process, the yield of the finally purified material to the starting material is very low and the vacuum pump is contaminated.

(2) The non-purified raw sample is scattered while the carrier gas is injected in a high vacuum, thus causing contamination. Further, the purified samples may be scattered when vacuum venting is performed in order to collect the purified organic materials after purification. Accordingly, the final purity of the target organic material is reduced.

(3) The vacuum environment of the entire system must be restored to normal pressure, after which the entire system must be stopped in order to collect the purified material after the purification process is finished. Accordingly, it is difficult to automate the entire system.

(4) Therefore, the purification process must be repeated, which increases energy consumption and thus increases the final cost of the organic material.

DISCLOSURE

Technical Problem

Accordingly, the present invention has been made keeping in mind the above problems occurring in the related art, and an object of the present invention is to provide a method and an apparatus for purifying an organic material using an ionic liquid by heating the organic material including an impurity to a sublimation point to generate a sublimated gas of the organic material, bringing the sublimated gas of the organic material into contact with the flowing ionic liquid to thus capture and dissolve the organic material, and recrystallizing the organic material. Thereby, the impurity and the highly pure organic material are simply separated and a large amount of the highly pure organic material is simply purified and produced.

Another object of the present invention is to provide an organic material purified using the purification method.

Technical Solution

In order to accomplish the above objects, the present invention provides a method of purifying an organic material using an ionic liquid, and the method includes a sublimation step of sublimating the organic material containing an impurity, a capturing step of bringing a sublimated gas of the organic material into contact with the flowing ionic liquid to capture the sublimated gas, and a recrystallization step of preferentially oversaturating the organic material, which is to be purified, of the sublimated gas, which is captured in the ionic liquid to be dissolved, to thus generate the recrystallized organic material.

Further, according to the present invention, the ionic liquid flows along the surfaces of a plurality of blades, which are disposed to cross the scattering path of the sublimated gas, during the capturing step.

Further, according to the present invention, the recrystallization step further includes a recirculation step of recirculating a mixture solution including the sublimated gas dissolved in the ionic liquid along the surfaces of the plurality of blades.

Further, according to the present invention, the plurality of blades are disposed at equal angles based on a vertical axis so that the ionic liquid flows downward along the surfaces of the plurality of blades.

Further, according to the present invention, the plurality of blades are disposed at equal angles based on a horizontal axis and rotate to enable the ionic liquid to flow.

Further, according to the present invention, the ionic liquid flows and falls down to cross the scattering path of the sublimated gas during the capturing step.

Further, according to the present invention, a recrystallization step further includes a recirculation step of recirculating a mixture solution, including the sublimated gas dissolved in the ionic liquid, to cross the scattering path of the sublimated gas.

Further, according to the present invention, a recrystallized organic material is separated to thus be collected and the mixture solution is circulated during the recirculation step.

Further, according to the present invention, the ionic liquid flows to thus be applied on the surface of at least one rotating roll, which is disposed to cross the scattering path of the sublimated gas, during the capturing step.

Further, according to the present invention, the method further includes removing a mixture solution, which includes the sublimated gas dissolved in the ionic liquid, from the surface of the rotating roll using a doctor blade.

In order to accomplish the above objects, the present invention also provides an apparatus for purifying an organic material using an ionic liquid, and the apparatus includes a sublimation unit sublimating the organic material containing an impurity, and a capturing unit which is disposed to communicate with the sublimation unit and brings a sublimated gas of the organic material into contact with the flowing ionic liquid to capture the sublimated gas. The organic material, which is to be purified, of the sublimated gas, which is captured in the ionic liquid to be dissolved, is preferentially oversaturated to thus generate the recrystallized organic material in the capturing unit.

Further, according to the present invention, the capturing unit includes a housing communicating with the sublimation unit, a plurality of blades disposed in the housing to cross the scattering path of the sublimated gas, an ionic liquid supply means supplying the ionic liquid so as to enable the ionic liquid to flow along the surfaces of the plurality of blades, and a storage means storing a mixture solution, which includes the sublimated gas dissolved in the ionic liquid, and the recrystallized organic material.

Further, according to the present invention, the ionic liquid supply means further includes a recirculation means recirculating the mixture solution from the storage means along the surfaces of the plurality of blades.

Further, according to the present invention, the plurality of blades are disposed at equal angles based on a vertical axis in a housing.

Further, according to the present invention, the plurality of blades are disposed at equal angles based on a horizontal axis in a housing, so as to rotate.

Further, according to the present invention, the capturing unit includes a housing communicating with the sublimation unit, an ionic liquid supply means supplying the ionic liquid so that the ionic liquid falls down to cross the scattering path of the sublimated gas, and a storage means storing a mixture solution, which includes the sublimated gas dissolved in the ionic liquid and the recrystallized organic material.

Further, according to the present invention, the ionic liquid supply means further includes a recirculation means recirculating the mixture solution from the storage means so that the mixture solution falls down to cross the scattering path of the sublimated gas.

Further, according to the present invention, the recirculation means further includes a collection means, which discharges the mixture solution and a recrystallized organic material from the storage means to an outside, separates the recrystallized organic material to collect the recrystallized organic material, and recirculates the mixture solution.

Further, according to the present invention, the capturing unit includes a housing communicating with the sublimation unit, at least one rotating roll disposed in the housing to cross a scattering path of the sublimated gas, and an ionic liquid storage unit disposed beneath the rotating roll to supply the ionic liquid to the surface of the rotating roll.

Further, according to the present invention, a doctor blade is provided at one side of the rotating roll to remove a mixture solution, including the sublimated gas dissolved in the ionic liquid, from the surface of the rotating roll.

In order to accomplish the above objects, the present invention also provides an organic material purified using the aforementioned purification method. The surface of the organic material is protected by a component from an ionic liquid.

Advantageous Effects

According to the present invention, it is not necessary to perform a process of carrying a sublimated gas, which is generated during a sublimation step, to implement reverse sublimation. Therefore, there is a merit in that the contamination of a purified sample by an inert carrier gas, which is used in a conventional sublimation purification method, is fundamentally avoided.

Further, in the present invention, since the sublimated gas, which is generated during the sublimation step, is not lost but the whole sublimated gas comes into contact with an ionic liquid to thus be captured and dissolved, the organic material may not be lost to the outside but may be wholly purified during a purification process, thereby increasing the purification yield to 95% or higher.

Further, in the present invention, only the target organic material is preferentially recrystallized in the ionic liquid to be deposited until an impurity is oversaturated to be recrystallized. Accordingly, the purity of the purified organic material may be rapidly and significantly increased to 99.95% or higher.

Further, in the present invention, the ionic liquid, which includes the organic material dissolved therein and the impurity, may be collected and then subjected to a separate purification process to thus be reused as the ionic liquid of the present invention. Accordingly, the ionic liquid may be used as an environmentally-friendly solvent and the purification cost may be reduced.

Further, in the present invention, the capacity of the apparatus may be controlled so as to add the organic material to the large amount of the ionic liquid until an oversaturation limit is reached to thus purify the large amount of the organic material, thereby significantly reducing the purification cost.

BEST MODE

Figure 1:
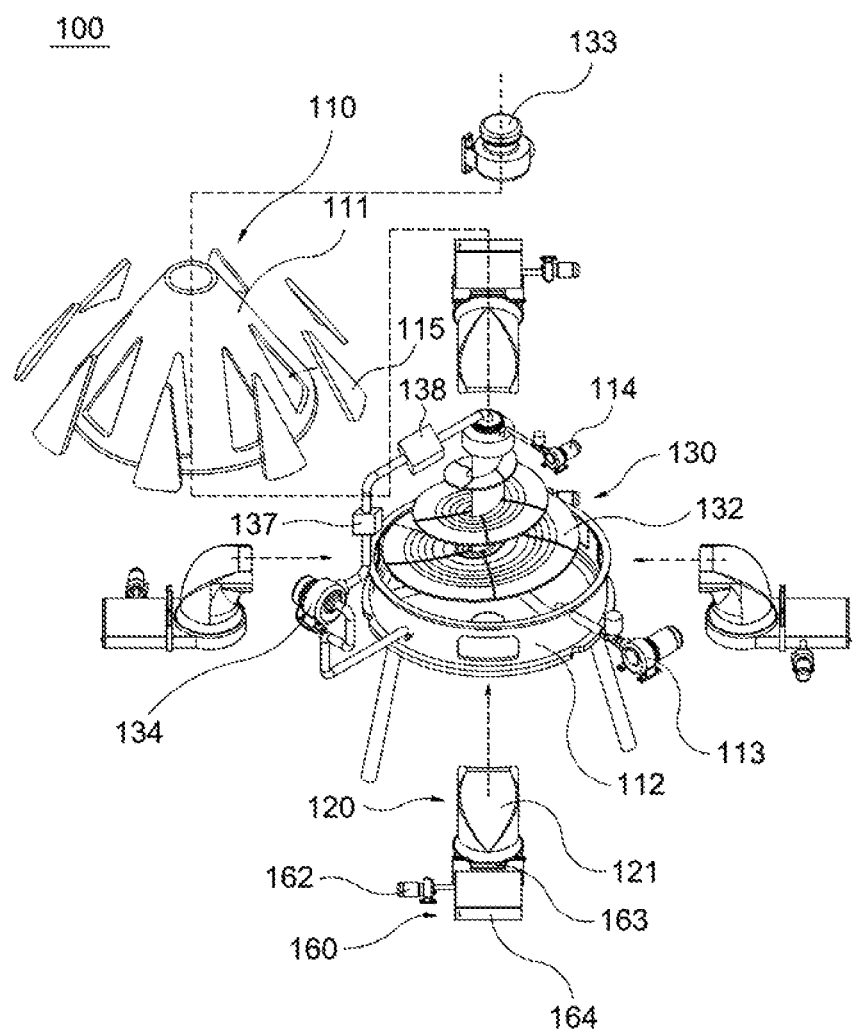
FIGS. 1 and 2 are an exploded perspective view and an assembly perspective view showing the constitution of a vertical-type apparatus for purifying an organic material using an ionic liquid according to a first embodiment of the present invention.

Hereinafter, preferred embodiments of a method and an apparatus for purifying an organic material using an ionic liquid according to the present invention will be described in detail with reference to the accompanying drawings.

An ionic liquid is a material, which is formed using the ionic bonding of cations and anions, like salt. The ionic liquid is present in a liquid state at 100° C. or less and is stably present in a liquid state even at high temperatures, and the vapor pressure of the ionic liquid is almost 0. Accordingly, ionic liquid is called a 'green solvent' and is attracting great attention as an environmentally-friendly solvent. Further, various inorganic materials, organic materials, and polymer materials may be dissolved in the ionic liquid, and the physicochemical properties of the ionic liquid, such as hydrophobicity, solubility, viscosity, and density, may be easily changed. Accordingly, the ionic liquid is also called a "designer solvent", and $10^{18}$ or more ionic liquids are theoretically capable of being synthesized to thus ensure the infinite potential as a solvent. That is, the ionic liquid has great advantages in that various properties, which are not obtained from a conventional organic solvent, are ensured and a solvent is capable of being selected and synthesized according to the requirements of a user (Recent trends of research for ionic liquid 1-Overview, Center for Advanced Bioseparation Technology in Inha University, Sang-hyeon Lee, Seong-ho Ha).

Meanwhile, physicochemical properties of the ionic liquid, such as non-volatility, non-combustibility, thermal stability, high ionic conductivity, electrochemical stability, and high boiling points, may be easily changed using a structural change of cations and anions, and accordingly, the ionic liquid has been in the limelight as a multifunctional 'designer solvent'. The ionic liquid may increase the activity and the stability of enzymes, a separation process thereof may be easily performed, and the ionic liquid is preferable in views of environmental and economic aspects. Accordingly, ionic liquids may be extensively used in various fields (Thi Phuong Thuy Pham, Chul-Woong Cho, Yeoung-Sang Yun, "Environmental fate and toxicity of ionic liquids: A review", Water Research, 44, 2010, pp. 352-372).

1-butyl-3-methylimidazolium bis(trifluoromethyl sulfonyl)imide (BMIM TFSI) of Chemical Formula 1 or 1-octyl-3-methylimidazolium bis(trifluoromethyl sulfonyl)imide (OMIM TFSI) of Chemical Formula 2 may be used as the ionic liquid according to the present embodiment. Alternatively, 1-ethyl-3-methylimidazolium bis(trifluoromethyl sulfonyl)imide (EMIM TFSI) may be used.

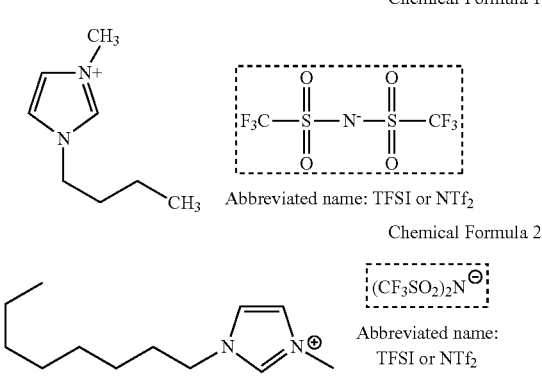

Chemical Formula 1

Chemical Formula 2

The ionic liquids (BMIM TFSI, OMIM TFSI, and EMIM TFSI) are a non-volatile organic solvent. The ionic liquids may be used to purify and recrystallize various organic materials, based on the mechanism whereby, when the dissolution and recrystallization of organic materials and impurities in the ionic liquid are repeated numerous times, the organic material, which is oversaturated earlier than other materials, is preferentially recrystallized.

Meanwhile, BMIM TFSI, OMIM TFSI, and EMIM TFSI have properties, such as low melting points, low vapor pressure, and non-flammabiliy, and include organic molecular ions, and the combination ratios of anions and cations thereof are controllable.

The ionic liquid according to the present embodiment is used to purify and recrystallize the organic material. The ionic liquid is stably present in a liquid phase at 100 to 120° C. under $10^{-7}$ Torr to thus be usable as a solvent even during a vacuum process.

Meanwhile, essential materials constituting an OLED may be broadly classified into a charge transport material (a hole injection layer, a hole transport layer, an electron injection layer, and an electron transport layer) and a light-emitting material (a fluorescent material, a phosphorescent material, and respective dopants). The total thickness of the OLED is about 100 to 200 nm and the OLED includes a ultra-thin film. Meanwhile, among the charge transport materials, examples of the hole transport material include NPB (N,N'-bis(naphthalene-1-yl)-N,N'-bis(phenyl)-benzidine), TPD (N,N'-bis-(2-methylphenyl)-N,N'-bis(phenyl)-benzidine), NPD (N,N'-di(naphthalene-1-yl)-N,N'-dibenzyl-benzidine), CuPc (copper phthalocyanine), and MTDATA (4,4',4''-tris(2-methylphenylamino)triphenylamine). Examples of the electron transport material include compounds such as $Alq_3$ (tri-(8-hydroxy-chinolinato)-aluminum) and DTVBi (4,4-bis(2,2-diphenyethen-1-yl)-diphenyl). Examples of the light-emitting material include Alq₃, coumarine derivatives, quinacridone derivatives, and rubrene.

Therefore, the NPB material may be used as the raw material of the organic material according to the present embodiment. NPB has a sublimation point of 180° C. or more. Therefore, when a loading boat containing the raw material of the organic material is heated to 200° C. or more, the raw material of the organic material is sublimated.

Meanwhile, in addition to the aforementioned materials, various materials are used as a deposition material (the raw material of the organic material), which is used to manufacture the OLED device. That is, in the present invention, various types of organic materials, which constitute the charge transport material or the light-emitting material of the OLED, may be used as the raw materials.

However, examples of the organic material include an organic TFT material, an organic solar battery material, and an organic semiconductor material, in addition to the low-molecular weight organic light-emitting material for use in the manufacture of the OLED device. Therefore, the present invention may be used to purify the organic material applied to the aforementioned various fields, but the organic material for OLEDs will be described by way of example below.

Hereinafter, preferred embodiments of an apparatus for purifying an organic material using an ionic liquid according to the present invention will be described in detail with reference to the accompanying drawings.

First Embodiment

Figure 2:
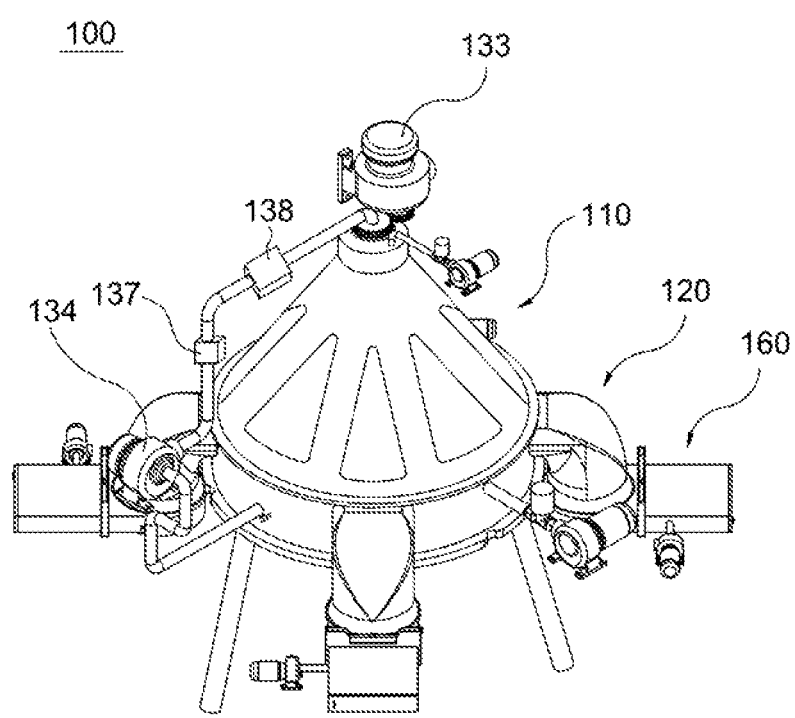
Figure 3:
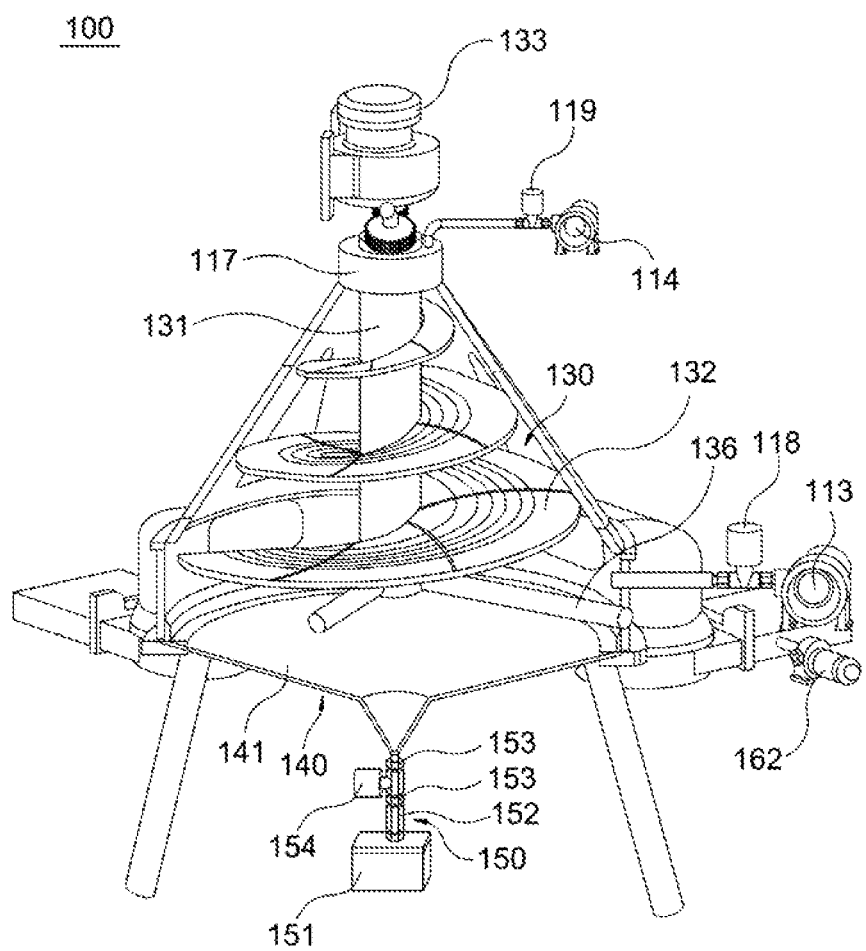
FIG. 3 is an assembly perspective view showing a portion of the apparatus for purifying the organic material shown in FIG. 2.
Figure 4:
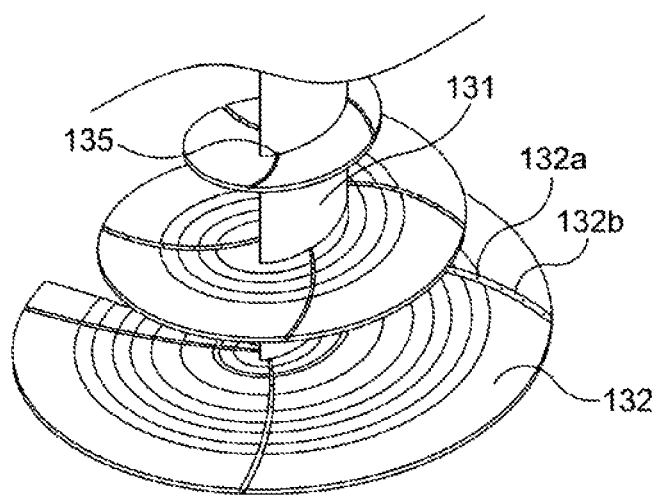
FIG. 4 is a detailed view specifically showing the constitution of a blade shown in FIG. 3.
Figure 5:
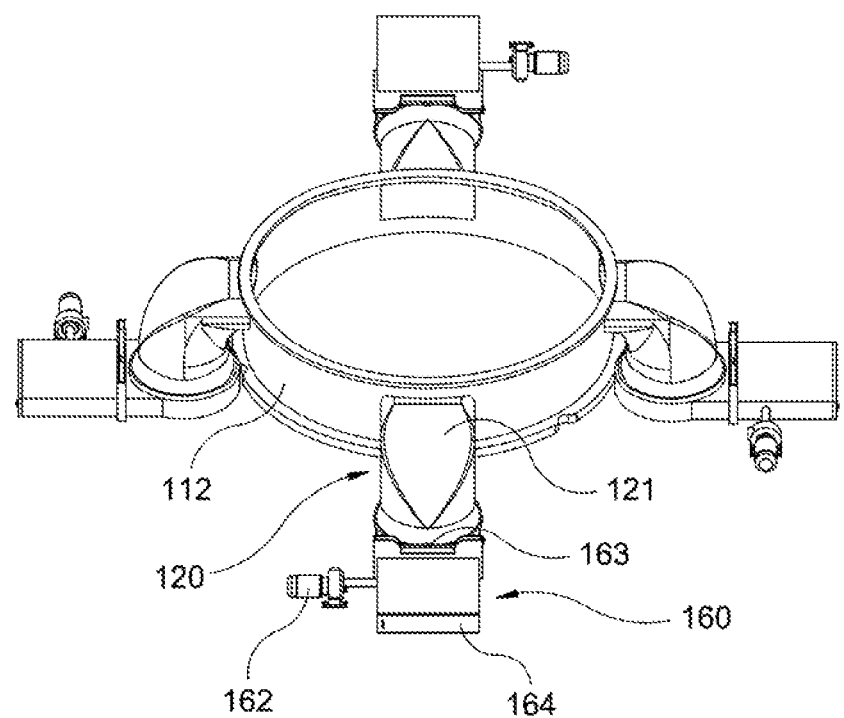
FIG. 5 is a detailed view specifically showing the combination relationship of the sublimation means shown in FIG. 1.
Figure 7:
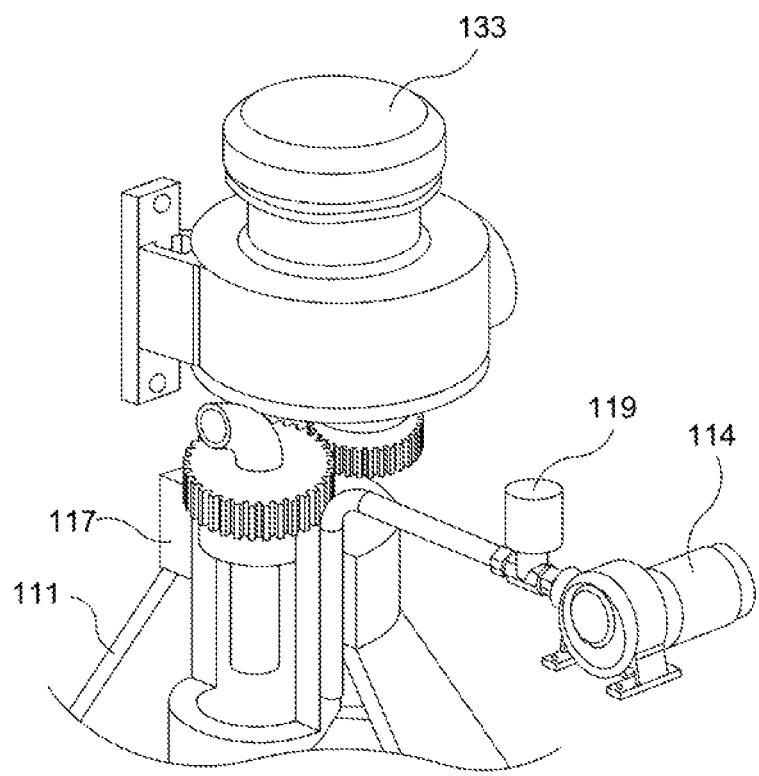
FIG. 7 is a detailed view showing the driving of a driving motor and the combination relationship of an upper end of a housing shown in FIG. 1.
Figure 8:
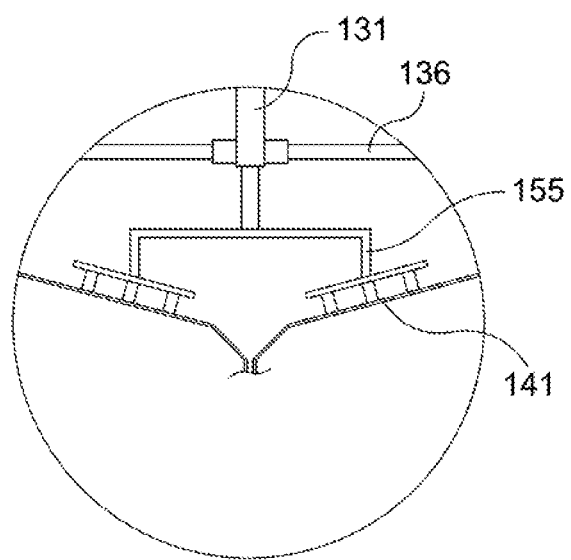
FIG. 8 is a conceptual view showing the collection means which is shown in FIG. 3 and is provided with an accumulation member.

FIGS. 1 and 2 are an exploded perspective view and an assembly perspective view showing the constitution of a vertical-type apparatus for purifying an organic material using an ionic liquid according to a first embodiment of the present invention, FIG. 3 is an assembly perspective view showing a portion of the apparatus for purifying the organic material shown in FIG. 2, FIG. 4 is a detailed view specifically showing the constitution of a blade shown in FIG. 3, and FIG. 5 is a detailed view specifically showing the combination relationship of a sublimation means shown in FIG. 1. In addition, FIG. 6 is a detailed view showing the replacement of the loading boat of the sublimation means shown in FIG. 5, FIG. 7 is a detailed view showing the driving of a driving motor and the combination relationship of an upper end of a housing shown in FIG. 1, and FIG. 8 is a conceptual view showing the collection means which is shown in FIG. 3 and is provided with an accumulation member.

As shown in FIG. 1, an apparatus 100 for purifying the organic material of the present embodiment broadly includes a sublimation unit sublimating the organic material for OLEDs, which contains an impurity, and a capturing unit which is disposed to communicate with the sublimation unit and brings the sublimated gas of the organic material into contact with the flowing ionic liquid to thus capture the sublimated gas. The organic material, which is a main component of the composition constitution and is to be purified, of the sublimated gas, which is captured in the ionic liquid to thus be dissolved, is preferentially oversaturated to thus generate the recrystallized highly pure organic material in the capturing unit.

As shown in FIGS. 1 to 4, the capturing unit includes a housing 110 having a predetermined internal volume in a vacuum atmosphere, a capturing means 130, which brings the sublimated gas of the organic material into contact with the ionic liquid to capture the sublimated gas, and a recrystallization means 140 preferentially oversaturating the organic material, which is a main component of the composition constitution and is to be purified, of the sublimated gas, which is captured in the ionic liquid by the capturing means 130 to thus be dissolved, thereby generating the recrystallized highly pure organic material.

Figure 6:
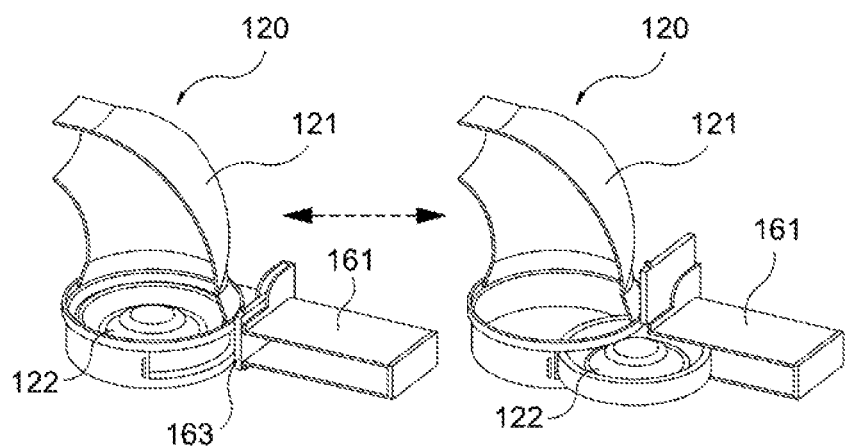
FIG. 6 is a detailed view showing the replacement of the loading boat of the sublimation means shown in FIG. 5.

In addition, as shown in FIGS. 5 and 6, the sublimation unit includes a plurality of sublimation means 120, which communicate with the lower part of the housing 110 to heat the raw material of the organic material for OLEDs containing the impurity to thus sublimate the raw material of the organic material.

Meanwhile, it is preferable that the apparatus 100 for purifying the organic material of the present embodiment further include a control means (not shown) controlling the operation of the sublimation means 120, the capturing means 130, and the recrystallization means 140.

The housing 110 is sealed from the outside and has a predetermined internal volume. The housing 110 includes an upper housing 111 constituting the upper part, a lower housing 112 combined with the lower part of the upper housing 111, a main vacuum pump 113 creating a vacuum in the housing 110, and an auxiliary vacuum pump 114 finely controlling the degree of vacuum in the housing 110.

The sublimation means 120 includes a sublimation chamber 121 combined with the lower housing 112, a loading boat 122 disposed in the sublimation chamber 121 to receive the raw material of the organic material, and a heater (not shown) heating the loading boat 122.

In addition, the capturing means 130 includes a hollow shaft 131 provided along the central axis of the housing 110, a screw-shaped blade 132 provided around the shaft 131, a driving motor 133 combined with the upper end of the shaft 131 to supply power, a pump 134 supplying the ionic liquid into the shaft 131, and a plurality of supply holes 135 formed in the shaft 131 to supply the ionic liquid along upper and lower surfaces of the blade 132 therethrough.

Hereinafter, the constitution of the housing 110 will be more specifically described with reference to FIGS. 1 to 4.

It is preferable that the upper housing 111 be conical. That is, it is preferable that the shape of the upper housing 111 be a cone having an inner diameter gradually increasing from the upper part to the lower part thereof. This is constituted in order to increase the contact area with the sublimated gas of the organic material, which is obtained using a plurality of sublimation means 120 combined with the lateral surface of the lower housing 112, at the lower part of the upper housing, thereby increasing the recrystallization efficiency of the sublimated gas. However, the shape of the upper housing 111 is not limited to the cone, but may be a cylinder or a prismatic type having a predetermined internal volume. Meanwhile, it is preferable that the upper housing 111 have a plurality of transparent windows 115 through which a recrystallization process performed in the housing is capable of being observed from outside. That is, the upper housing 111 may consist mostly of stainless steel and may have transparent windows 115 in some portions thereof. The transparent windows 115 may be made of a glass material. Meanwhile, the entire upper housing 111 may be made of a transparent glass material.

In addition, the upper housing 111 is provided with a heater (not shown) controlling the internal temperature of the upper housing 111. The heater may be provided on the surface of stainless steel constituting the upper housing 111 and, for example, a plane heater may be provided. However, when the entire upper housing 111 is made of the transparent glass material, band-shaped heaters are preferably provided around the upper housing 111 at predetermined intervals. This is constituted in order to observe the inside of the housing 110 at predetermined intervals even when the heaters are provided at the upper housing 111. The disposed heater serves to heat the ionic liquid and control the temperature of the internal atmosphere of the upper housing 111, thereby controlling the solubility of the sublimated gas of the organic material dissolved in the ionic liquid.

Meanwhile, preferably, in the apparatus 100 for purifying the organic material of the present embodiment, infrared rays are radiated through the transparent windows 115, which are provided in the external side of the upper housing 111, to heat the shaft 131 and the blade 132 to thus control the internal temperature of the upper housing 111. Alternatively, hot wires may be provided in the shaft 131 and the blade 132 to control the internal temperature of the upper housing 111.

The lower housing 112 is combined with the lower part of the upper housing 111 and has a cylindrical shape. Meanwhile, the lower housing 112 has a storage tank (storage means) 141, in which the ionic liquid used to recrystallize the organic material, the ionic liquid (mixture solution) including the sublimated gas dissolved therein, and the recrystallized organic material are collected, at the lower part thereof. The storage tank 141 is formed by a portion of the lower part of the lower housing 112 so as to constitute a portion of the constitutional elements of the recrystallization means 140, and the storage tank 141 may have a predetermined volume. Meanwhile, the storage tank 141 is preferably tapered downward so that the ionic liquid and the recrystallized organic material are more easily collected at the center spot.

In addition, the lower housing 112 is provided with a heater (not shown) controlling the internal temperature of the lower housing 112 and the temperature of the ionic liquid and the recrystallized organic material stored in the storage tank 141. The heater may be provided on the surface (including the lower surface) of the stainless steel constituting the lower housing 112, and, for example, a plane heater may be provided.

The main vacuum pump 113 serves to create a vacuum in the housing 110 and communicates with one side of the lower housing 112 through a vacuum pipe. In addition, the auxiliary vacuum pump 114 serves to finely control the degree of vacuum in the housing 110 and communicates with one side of a sealing member 117, sealing the upper housing 111, through a vacuum pipe. Throttle valves 218 and 219 are provided in the vacuum pipes of the vacuum pumps 113 and 114.

Hereinafter, the constitution of the sublimation means 120 will be more specifically described with reference to FIGS. 5 and 6.

The sublimation chamber 121 communicates with the lower housing 112, has a size sufficiently large to receive the loading boat 122, and is structured so that the sublimated gas of the organic material smoothly flows to the lower housing 112 therethrough. That is, the sublimation chamber 121 has a wide lower part, at which the loading boat 122 is positioned, and a narrow upper part communicating with the lower housing 112.

Meanwhile, a shutter (not shown) may be further provided in the sublimation chamber 121 so as to collect the sublimated gas of the organic material, sublimated in the loading boat 122, and to then enable the collected gas to flow to the lower housing 112 at once. Further, preferably, a heater (not shown), such as a plane heater, is further provided on the external surface of the sublimation chamber 121 so as to heat the inside of the sublimation chamber 121, thereby more effectively sublimating the raw material of the organic material in the loading boat 122 and preventing the sublimated gas of the organic material from being recrystallized on the internal surface of the sublimation chamber 121.

The loading boat 122 is positioned at the lower part of the sublimation chamber 121, and a heater (heating means, not shown) is provided at the lower part of the loading boat 122. Further, the loading boat 122 has the upper part, which receives the raw material of the organic material to be purified. Meanwhile, the loading boat 122 may include a receiving part, which receives the raw material of the organic material and which has a shape, including a plurality of protrusions (comb shape), or a wave shape so as to uniformly heat the raw material of the organic material, that is, increase a contact area.

The heater (heating means) serves as a heat source sublimating the raw material of the organic material in the loading boat 122, and adopts electric heating, electromagnetic heating, or electronic beam heating modes. For example, thermal evaporation, laser beams, microwaves, or magnetic heating may be applied as an alternative mode. When the raw material of the organic material is sublimated using the heater or other mode, preferably, heating is performed from low temperatures just before the sublimation point, is paused for 1 to 5 min, and then continues to the sublimation point or higher, thereby sublimating the raw material of the organic material.

Hereinafter, the constitution of the capturing means 130 will be more specifically described with reference to FIGS. 1 to 4, 7, and 8.

The shaft 131 is hollow and provided along the central axis of the housing 110. The upper and lower ends of the shaft 131 are rotatably combined with and supported by the upper and lower parts of the housing 110. That is, the upper end of the shaft 131 is rotatably combined with and supported by the sealing member 117, sealing the upper part of the upper housing 111, and the lower end of the shaft 131 is rotatably combined with and supported by a support member 136 fixed to the internal surface of the lower housing 112. Preferably, the support member 136 is positioned beneath the portion of the housing that communicates with the sublimation chamber 121 so that the sublimated gas of the organic material rarely comes into contact with the support member 136.

The blades 132 has a screw shape around the shaft 131. Since the housing 110 has a conical shape, the blades 132, corresponding in shape to the housing, have a width gradually increasing from the upper part to the lower part thereof. That is, the blade 132 is disposed in the housing 110 to cross the scattering path of the sublimated gas. The blades are disposed at equal angles based on the vertical axis in the housing 110. Meanwhile, when the housing 110 is cylindrical, the width of the blade 132 may be constant. Meanwhile, it is preferable that the edge of the blade 132 almost come into contact with the internal surface of the housing 110. That is, it is preferable that the blades 132 rotate while being in contact with the internal surface of the housing 110. This is constituted in order to apply the ionic liquid, flowing along the blade 132, on the entire internal surface of the housing 110 and to more effectively separate and collect the organic material recrystallized on the internal surface of the housing 110.

Meanwhile, the blade 132 has the screw shape rotating clockwise from the upper part thereof downward. This is constituted in order to enable the sublimated gas of the organic material to smoothly flow from the lower part to the upper part in the housing 110. Therefore, the blade 132 serves as a fluidizing unit fluidizing the sublimated gas of the organic material. However, since the blade 132 has the aforementioned constitution, the ionic liquid, flowing along the upper and lower surfaces of the blade 132, may receive fluidizing force toward the upper part of the housing 110. However, the rotation force attributable to the rotation of the blade 132 is enough to fluidize the sublimated gas but not enough to fluidize the ionic liquid. Accordingly, there is no fear of fluidizing the ionic liquid to the upper part of the housing 110.

Further, the blade 132 may further have a plurality of holes 132a that serve to reduce the force of fluidizing the ionic liquid to the upper part of the housing 110 and serve as a path through which the ionic liquid flows to the lower part. Further, the blade 132 may further have a plurality of curved grooves 132b, guiding the ionic liquid to smoothly flow to the lower part of the housing 110 (see FIG. 4).

Meanwhile, the blade 132 may be constituted by a plurality of turbine blades, which are disposed at predetermined intervals in a longitudinal direction to be fixed to the shaft 131, rather than the aforementioned continuous screw type. That is, the blade 132 may be a discontinuous type to thus fluidize the ionic liquid downward through gaps thereof. When the blade 132 is the discontinuous type, the plurality of holes 132a or the plurality of curved grooves 132b does not need to be provided in order to fluidize the ionic liquid to the lower part.

The driving motor 133 is combined with the upper end of the shaft 131 to provide power, and includes a typical motor. The driving motor 133 engages with the upper end of the shaft 131 (see FIG. 7).

The pump 134 serves to supply the ionic liquid into the shaft 131 and to supply the ionic liquid from the outside and/or the ionic liquid (mixture solution) used to recrystallize the organic material. Therefore, the pump 134 is connected to an inflow path (not shown), through which the fresh ionic liquid flows in, a circulation pipe, through which the ionic liquid is circulated, and a supply pipe, through which the fresh ionic liquid and/or the reused ionic liquid are supplied to the shaft 131. The pump 134 and the pipes serve as an ionic liquid supply means, fluidizing the ionic liquid through the inside of the shaft 131 along the surface of the blade. Further, the pump 134 is a recirculation means that recirculates the mixture solution, collected in the storage tank 141, to the capturing means 130. The recirculation means is used as a constitutional element of the recrystallization means 140, which repeatedly brings the mixture solution into contact with the sublimated gas to thus oversaturate the organic material in the ionic liquid, thereby recrystallizing the organic material. The supply pipe communicates with one side of the shaft 131, and the circulation pipe communicates with the storage tank 141 of the housing 110. Meanwhile, the recirculation means recirculates the mixture solution through the elements outside the housing while the pump 134 is disposed outside the housing 110 in the present embodiment, but may recirculate the mixture solution through the shaft 131 while the pump is disposed in the housing 110. When the aforementioned internal circulation structure is ensured, a vacuum condition may not be separately considered, and accordingly, the constitution may be simplified.

The recirculation means may further include a collection means, which discharges the mixture solution and the recrystallized organic material from the storage tank 141 to the outside of the storage tank 141, separates the recrystallized organic material to collect the recrystallized organic material, and recirculates the mixture solution. The collection means includes a collection container 137, which separates the recrystallized organic material from the mixture solution, supplied through the supply pipe using the pump 134, and which stores the separated organic material, and a circulation pump 138, recirculating the mixture solution, separated from the collection container 137, to the capturing means 130. The collection container 137 includes a device for separating the recrystallized organic material using filtration or centrifugation. The collection means is suitably used in the case where the recrystallized organic material is not precipitated downward in the ionic liquid but floats on the surface of the ionic liquid or is mixed in the ionic liquid.

Meanwhile, a plurality of supply holes 135 are formed in the shaft 131 to supply the ionic liquid along the upper and lower surfaces of the blade 132 therethrough (see FIG. 4). The plurality of supply holes 135 are formed at predetermined intervals along the blade 132. The plurality of supply holes 135 are formed in either surface of the upper and lower surfaces of the blade 132 so as to supply the ionic liquid along the upper and lower surfaces of the blade 132 therethrough. The plurality of supply holes 135 serve as nozzles for spraying the ionic liquid when pressure is applied to the ionic liquid. It is preferable that the supply holes 135 be constituted so as to spray the ionic liquid like a diffusion nozzle.

In the capturing means 130 according to the present embodiment, the ionic liquid is supplied under a predetermined pressure into the shaft 131 using the pump 134, and the shaft 131 is rotated by driving force from the driving motor 133 to supply the ionic liquid to the upper and lower surfaces of the blade 132, thereby applying the ionic liquid on the upper and lower surfaces of the blade 132 and on the entire internal surface of the housing 110. That is, the capturing means 130 of the present embodiment supplies the ionic liquid according to a forcible fluidization method using the driving force from the driving motor 133.

However, the capturing means 130 may adopt a non-forcible fluidization method using gravity instead of the forcible fluidization method. Generally, the ionic liquid has a predetermined viscosity. Therefore, the ionic liquid may be supplied using the aforementioned characteristic of the ionic liquid so that the ionic liquid flows along the upper surface and/or the lower surface of the blade 132.

Further, the apparatus 100 for purifying the organic material of the present embodiment may be controlled so that the sublimated gas smoothly moves to the upper part due to the difference in the degree of vacuum in the housing 110 or a separate carrier gas, such as an inert gas, using a main vacuum pump 113 and/or an auxiliary vacuum pump 114. When the carrier gas is used, a carrier gas supply source and a discharge pump may be respectively provided at one side and the other side of the housing 110.

Meanwhile, the apparatus 100 for purifying the organic material of the present embodiment may further include a collection means 150, which collects the purified organic material precipitated on the bottom of the storage tank 141, and a replacement means 160 replacing an empty loading boat, from which the raw material of the organic material is sublimated, with a new loading boat receiving the raw material of the organic material.

The collection means 150 includes a collection box 151, which is connected to a connection line 152 formed beneath the storage tank 141, two valves 153, which are provided at predetermined intervals along a connection line 152 between the storage tank 141 and the collection box 151 to control the movement of the ionic liquid, and a vacuum pump 154, which is provided between the two valves 153 to create a vacuum in the connection line 152. The collection box 151 is removably combined with the connection line 152.

Therefore, the purified and deposited organic material gradually piles higher in the collection box 151. Further, when the amount of the piled organic material reaches a predetermined value in the collection box 151, the two valves 153 may be closed and the collection box 151 may be removed from the connection line 152 to collect the organic material. Meanwhile, when a new collection box 151 is connected to the connection line 152, after the new collection box 151 is fastened to the connection line 152, the valve 153 adjacent to the collection box 151 is opened. Subsequently, a vacuum is created in the connection line 152 using the vacuum pump 154, and the remaining valve 153 is then opened.

Further, the collection means 150 may further include an accumulation member 155 collecting the recrystallized organic material, precipitated on the bottom of the storage tank 141, in the collection box 151 (see FIG. 8). The accumulation member 155 is combined with the lower part of the shaft 131 to be rotated by the power of the shaft 131. Meanwhile, a scraper may be used as the accumulation member 155. The collection means 150 is suitably used in the case where the recrystallized organic material is precipitated downward in the ionic liquid.

The replacement means 160 includes a chamber 161, which is selectively opened and closed with respect to one side of the sublimation chamber 121 and the outside under atmospheric pressure so that the new loading boat is received in the chamber and the empty loading boat is drawn from the chamber, a vacuum pump 162, which creates a vacuum in the chamber 161, and opening and closing devices 163 and 164, which selectively open and close the chamber 161 with respect to one side of sublimation chamber 121 and the outside under atmospheric pressure.

Meanwhile, in the replacement means 160, the chamber 161 may be constituted by a load lock chamber, which is typically used in LCD devices. The replacement means 160 may include a movable robot (not shown), which is provided in the load lock chamber so as to move the loading boat to the housing 110, the load lock chamber, or the outside under atmospheric pressure, thereby automatically replacing the loading boat.

Figure 9:
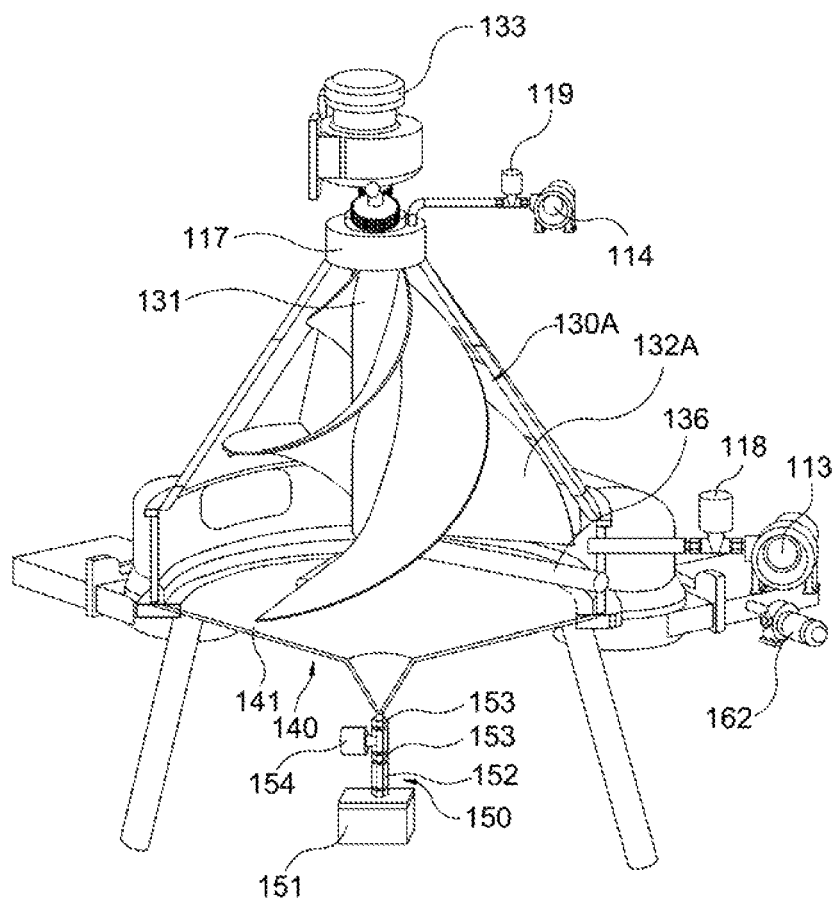
FIG. 9 is an assembly perspective view showing a portion of the apparatus for purifying the organic material, the apparatus including a modified example of the capturing means shown in FIG. 1.

FIG. 9 is an assembly perspective view showing a portion of the apparatus for purifying the organic material, the apparatus including a modified example of a capturing means shown in FIG. 1. As shown in FIG. 9, a capturing means 130A of a modified example includes a plurality of blades 132A, which is provided around the shaft 131, and the remaining constitutional elements, which are the same as those of the capturing means 130. The blades 132A are arranged in a longitudinal direction to have a turning angle in a clockwise direction from the upper part thereof downward. That is, the phase difference between one end and the other end of the blade 132A has a turning angle of, for example, about 120°. Therefore, the plurality of blades 132A are disposed at equal angles, based on a vertical axis, in the housing 110 to cross the scattering path of the sublimated gas.

Figure 10:
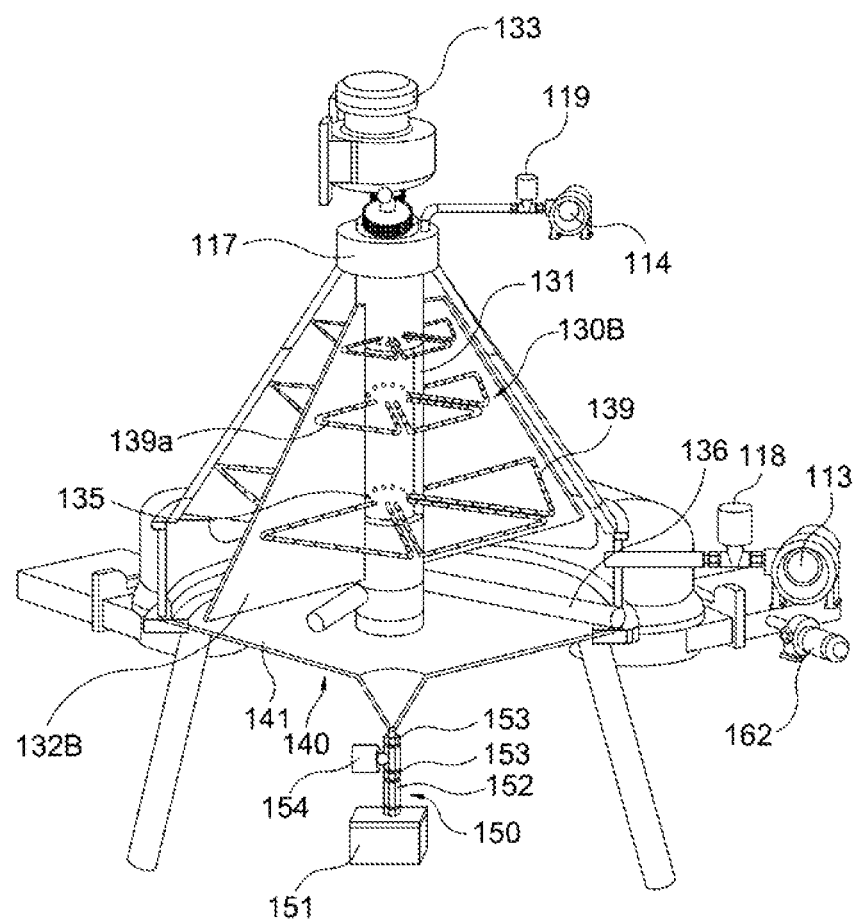
FIG. 10 is an assembly perspective view showing a portion of the apparatus for purifying the organic material, the apparatus including another modified example of the capturing means shown in FIG. 1.

FIG. 10 is an assembly perspective view showing a portion of the apparatus for purifying the organic material, the apparatus including another modified example of the capturing means shown in FIG. 1. As shown in FIG. 10, a capturing means 130B of another modified example includes a plurality of blades 132B, which are provided at equal intervals in a longitudinal direction around the shaft 131, a plurality of spray pipes 139, which communicate with the plurality of supply holes 135 to spray the ionic liquid, supplied to the shaft 131, on the surfaces of the blades 132B and on the internal surface of the upper housing 111 therethrough, and the remaining constitutional elements, which are the same as those of the capturing means 130. The blades 132B are provided at equal intervals in a longitudinal direction around the shaft 131 and rotate on the scattering path of the sublimated gas. That is, the plurality of blades 132B are disposed at equal angles, based on a vertical axis, in the housing 110 to cross the scattering path of the sublimated gas.

In addition, the spray pipes 139 are disposed in a longitudinal direction between the blades 132B while forming a triangle so as to uniformly spray the ionic liquid on the surfaces of the blades 132B and on the internal surface of the upper housing 111. A plurality of spray holes 139a are formed in the spray pipes 139 to spray the ionic liquid therethrough. Preferably, the spray holes 139a may face the surfaces of the blades 132B and the internal surface of the upper housing 111, and the ionic liquid may be sprayed through the spray holes 139a like a diffusion nozzle.

Hereinafter, a method of purifying the organic material using the apparatus for purifying the organic material of the present embodiment will be described.

First, the loading boat 122, receiving the raw material of the organic material, is provided in the sublimation chamber 121, and the pump 134 and the driving motor 133 are driven to apply the ionic liquid on the upper and lower surfaces of the blade 132 and on the entire internal surface of the housing 110. Subsequently, a vacuum is created in the housing 110 and in the sublimation chamber 121 using the main vacuum pump 113.

Next, the loading boat 122 is heated to just below the sublimation point of the raw material of the organic material using the heater, is left for 1 to 5 min, and is further heated to the sublimation point or higher. Accordingly, the sublimated gas of the organic material is obtained. The sublimated gas includes the organic material and impurities. Meanwhile, the ionic liquid flows along the upper and lower surfaces of the blade 132 from the time when the sublimated gas of the organic material is formed. That is, the ionic liquid is supplied into the shaft 131 under a predetermined pressure using the pump 134, and the shaft 131 rotates due to the driving force of the driving motor 133 to enable the ionic liquid to flow along the upper and lower surfaces of the blade 132. Further, the heater, provided on the external surface of the housing 110, is used to increase the internal temperature of the housing 110 to the temperature at which the organic material is easily recrystallized.

The ionic liquid flows along the upper and lower surfaces of the blade 132. The sublimated gas of the organic material flows into the housing 110 when the shutter is opened and is naturally scattered through the blade 132 to the upper part of the housing 110 to thus come into contact with the ionic liquid at the upper and lower surfaces of the blade 132. The sublimated gas is captured in the ionic liquid due to the contact and is then gradually dissolved to be recrystallized, thus being collected in the storage tank 141 at the lower part of the housing 110. That is, when the sublimated gas is dissolved in the ionic liquid, the content of the organic material to be purified is totally higher than that of the impurity. Accordingly, the organic material is preferentially oversaturated to thus commence recrystallization first. Thereby, the high-purity organic material is deposited.

Meanwhile, the solubility of the sublimated gas dissolved in the ionic liquid may be controlled using the heater provided on the external surface of the upper housing 111 and the lower housing 112. Therefore, the solubility of the sublimated gas to the ionic liquid may be controlled to thus control the degree of oversaturation and the recrystallization rate of the organic material in the ionic liquid. Therefore, mixing with the impurity may be minimized during the recrystallization process, and the high-purity organic material, deposited in the ionic liquid, may be appropriately collected from the storage tank 141 of the housing 110.

For example, when the recrystallized organic material is precipitated downward in the ionic liquid, the purified organic material may be collected using the collection box 151 of the collection means 150 connected to the storage tank 141. However, when the recrystallized organic material is not precipitated downward in the ionic liquid but floats on the surface of the ionic liquid or is mixed in the ionic liquid, after the mixture solution and the recrystallized organic material are discharged from the storage tank 141 to the outside of the storage tank 141, the recrystallized organic material may be separated using filtration or centrifugation to thus be collected in the collection container 137, and then the mixture solution may be recirculated into the capturing means 130 using the circulation pump 138.

Meanwhile, when the raw material of the organic material is completely sublimated in the loading boat 122, the loading boat 122 may be replaced with a new loading boat, containing the raw material of the organic material, using the replacement means 160. The organic material may be continuously purified according to the aforementioned procedure.

After the high-purity organic material, which is deposited in the ionic liquid, is collected, the organic material, which was included in the sublimated gas, is dissolved and thereby oversaturated in the ionic liquid, and a small amount of the impurity remains in the ionic liquid. Further, as the purification process progresses, the content of the impurity in the ionic liquid is increased, and the impurity components are oversaturated after a predetermined time. Accordingly, the impurity is mixed with the recrystallized organic material. In this case, it is preferable to replace the ionic liquid, used during the purification process, with the high-purity ionic liquid.

Second Embodiment

Figure 11:
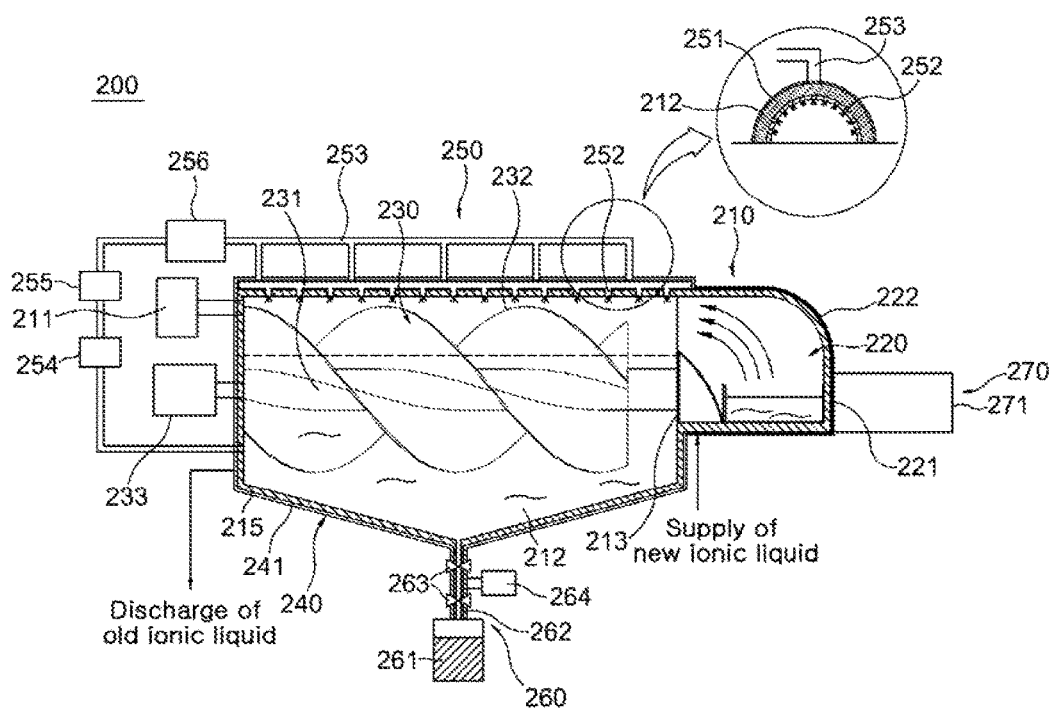
FIG. 11 is a conceptual view showing the constitution of a horizontal-type apparatus for purifying an organic material using an ionic liquid according to a second embodiment of the present invention.

FIG. 11 is a conceptual view showing the constitution of a horizontal-type apparatus for purifying an organic material using an ionic liquid according to a second embodiment of the present invention. As shown in FIG. 11, an apparatus 200 for purifying an organic material of the present embodiment is the same as the apparatus 100 for purifying the organic material of the first embodiment, except that a plurality of blades are disposed at equal angles to rotate based on the horizontal axis in the housing. Therefore, the description of the overlapping portion of the present embodiment with the first embodiment will be omitted.

A housing 210 has a predetermined internal volume to be sealed from the outside, and is provided with a vacuum pump 211 creating a vacuum in the housing 210. A sublimation means 220 includes a loading boat 221, receiving the raw material of the organic material, and a heater (not shown) heating the loading boat 221. In addition, a capturing means 230 includes a shaft 231, provided along the horizontal central axis of the housing 210, a plurality of blades 232, provided around the shaft 231, and a driving motor 233 combined with an end of the shaft 231 to provide power.

Hereinafter, the constitution of the housing 210 will be more specifically described.

The housing 210 has a predetermined internal volume to thus be sealed from the outside, and preferably has a cylindrical shape having a predetermined length. Meanwhile, the housing 210 includes a partition 213, serving as a storage tank (storage means) 241 storing the ionic liquid 12 therein. Therefore, the housing 210 has a space, including the loading boat 221, and another space, including the storage tank 241 storing the ionic liquid 212.

Meanwhile, it is preferable that the housing 210 have a plurality of transparent windows (not shown) through which a recrystallization process performed in the housing is capable of being observed from the outside. That is, the housing 210 may consist mostly of stainless steel and may have transparent windows (not shown) in some portions thereof. The transparent windows may be made of a glass material. Meanwhile, the entire housing 210 may be made of a transparent glass material.

In addition, the housing 210 is provided with a heater 215 controlling the internal temperature of the housing 210. The heater 215 may be provided on the surface of stainless steel constituting the housing 210 and, for example, a plane heater may be provided. However, when the entire housing 210 is made of the transparent glass material, band-shaped heaters 215 are preferably provided around the housing 210 at predetermined intervals. This constitution is disposed in order to observe the inside of the housing 210 at predetermined intervals even when the heaters 215 are provided at the housing 210.

The disposed heater 215 serves to heat the ionic liquid and control the temperature of the internal atmosphere of the housing 210, thereby controlling the solubility of the sublimated gas of the organic material dissolved in the ionic liquid. Further, the heater 215 also serves to control the temperature of the ionic liquid (mixture solution), which includes the sublimated gas dissolved therein and which is collected in the storage tank 241, thereby more smoothly depositing the organic material to recrystallize. A plurality of heaters 215 may be provided to control the temperature of each part.

Meanwhile, preferably, in the apparatus 200 for purifying the organic material of the present embodiment, infrared rays are radiated through the transparent windows, which are provided in the external side of the housing 210, to heat the shaft 231 and the blade 232 to thus control the internal temperature of the housing 210.

Further, the housing 210 has the storage tank 241, which stores the ionic liquid 212 and which is formed by the partition 213, at the lower part thereof. The storage tank 241 forms a portion of the constitutional elements of a recrystallization means 240, and serves to store fresh ionic liquid 212 and the ionic liquid used to recrystallize the organic material, and also serves as a collection tank collecting the ionic liquid (mixture solution), including the sublimated gas dissolved therein, and the recrystallized organic material. The storage tank 241 may be formed by a portion of the lower part of the housing 210 and may have a predetermined volume. Meanwhile, the storage tank 241 is preferably tapered downward so that the ionic liquid, including the sublimated gas dissolved therein, and the recrystallized organic material are more easily collected at the center spot.

The vacuum pump 211 serves to create a vacuum in the housing 210 and communicates with one side of the housing 210 through a vacuum pipe. Meanwhile, it is preferable that a throttle valve be further provided in the vacuum pipe of the vacuum pump 211.

Hereinafter, the constitution of the sublimation means 220 will be more specifically described.

The sublimation means 220 is disposed at one side of the housing 210 to heat the raw material of the organic material for OLEDs, including impurities, thus sublimating the raw material of the organic material. Preferably, a heater 222, such as a plane heater, is further provided on the external surface of the housing 210 so as to more effectively sublimate the raw material of the organic material in the loading boat 221 and to prevent the sublimated gas of the organic material from being recrystallized on the internal surface of the housing 210.

The loading boat 221 is positioned at a portion of the lower part of the housing 210, and a heater (heating means, not shown) is provided at the lower part of the loading boat 221. Further, the loading boat 221 has the upper part, receiving the raw material of the organic material to be purified. Meanwhile, the loading boat 221 may include a receiving part, which receives the raw material of the organic material and which has a shape including a plurality of protrusions (comb shape) or a wave shape so as to uniformly heat the raw material of the organic material, that is, increase a contact area.

The heater (heating means) serves as a heat source sublimating the raw material of the organic material in the loading boat 221, and adopts electric heating, electromagnetic heating, and electronic beam heating modes. For example, thermal evaporation, laser beams, microwaves, or magnetic heating may be applied as an alternative mode. When the raw material of the organic material is sublimated using the heater and other modes, preferably, heating is performed from low temperatures just before the sublimation point, is paused for 1 to 5 min, and then continues to the sublimation point or higher, thereby sublimating the raw material of the organic material.

Hereinafter, the constitution of the capturing means 230 will be more specifically described.

The shaft 231 is provided along the horizontal central axis of the housing 210. An end of the shaft 231 is rotatably supported by the partition 213, and the other end thereof is rotatably supported by the housing 210.

The blade 232 is provided around the shaft 231 in a horizontal direction. The phase difference between one end and the other end of the blade 232 has a turning angle of, for example, about 120°. Therefore, a plurality of blades 232 are disposed at equal angles, based on a horizontal axis, in the housing 210 to thus cross the scattering path of the sublimated gas. Meanwhile, it is preferable that the edge of the blade 232 almost come into contact with the internal surface of the housing 210 other than a portion of the lower part of the housing 210. That is, it is preferable that the blade 232 rotate while being in contact with the internal surface of the housing 210. This is constituted in order to apply the ionic liquid, flowing along the blade 232, on the entire internal surface of the housing 210 and to more effectively separate and collect the organic material recrystallized on the internal surface of the housing 210.

The driving motor 233 is combined with one end of the shaft 231 to provide power, and includes a typical motor.

Meanwhile, the apparatus 200 for purifying the organic material of the present embodiment may further include a spray means 250, which sprays the ionic liquid downward on a lateral path of the flowing sublimated gas, a collection means 260, which collects the purified organic material, recrystallized and precipitated on the bottom of the storage tank 241 of the housing 210, and a replacement means 270 replacing an empty loading boat, from which the raw material of the organic material is sublimated, with a new loading boat for receiving the raw material of the organic material. The spray means 250 serves as an ionic liquid supply means, which supplies the ionic liquid so that the ionic liquid falls down to cross the scattering path of the sublimated gas.

The spray means 250 includes a receiving unit 251, which has a predetermined receiving space between the external upper surface of the housing 210 and the receiving unit, a plurality of communication holes 252, through which the receiving unit 251 communicates with the housing 210, a connection pipe 253, through which the receiving unit 251 is connected to the storage tank 241, and a pump 254, which is provided in the connection pipe 253 to spray the ionic liquid 212 from the storage tank 241 through the receiving unit 251 and the plurality of communication holes 252 in the lateral path of the flowing sublimated gas downward. The pump 254 is a recirculation means for recirculating the mixture solution, collected in the storage tank 241, into the capturing means 230. The recirculation means is used as a constitutional element of the recrystallization means 240, which repeatedly brings the mixture solution into contact with the sublimated gas to oversaturate the organic material in the ionic liquid, thereby recrystallizing the organic material. In addition, the communication holes 252 serve as nozzles for spraying the ionic liquid when pressure is applied to the ionic liquid using the pump 254. It is preferable that the communication holes 252 be constituted so as to spray the ionic liquid like a diffusion nozzle.

The recirculation means may further include a collection means, which discharges the mixture solution and the recrystallized organic material from the storage tank 241 to the outside of the storage tank 241, separates the recrystallized organic material to collect the recrystallized organic material, and recirculates the mixture solution. The collection means includes a collection container 255, which separates the recrystallized organic material from the mixture solution, supplied through the connection pipe 253 using the pump 254, and which stores the separated organic material, and a circulation pump 256 recirculating the mixture solution, separated from the collection container 255, to the capturing means 230. The collection container 255 includes a device for separating the recrystallized organic material using filtration or centrifugation. The collection means is suitably used in the case where the recrystallized organic material is not precipitated downward in the ionic liquid but floats on the surface of the ionic liquid or is mixed in the ionic liquid.

Meanwhile, another collection means 260 includes a collection box 261, which is connected to a connection line 262 formed beneath the storage tank 241, two valves 263, which are provided at a predetermined interval in the connection line 262 between the storage tank 241 and the collection box 261 to control the movement of the ionic liquid, and a vacuum pump 264, which is provided between the two valves 263 to create a vacuum in the connection line 262. The collection box 261 is removably combined with the connection line 262.

Therefore, the purified and deposited organic material gradually piles higher in the collection box 261. Further, when the amount of the piled organic material reaches a predetermined value in the collection box 261, the two valves 263 may be closed and the collection box 261 may be removed from the connection line 262 to collect the organic material. Meanwhile, when the new collection box 261 is connected to the connection line 262, after the new collection box 261 is fastened to the connection line 262, the valve 263 adjacent to the collection box 261 is opened. Subsequently, a vacuum is created in the connection line 262 using the vacuum pump 264, and the remaining valve 263 is then opened. The collection means 260 is suitably used in the case where the recrystallized organic material is precipitated downward in the ionic liquid.

The replacement means 270 includes a chamber 271, which is selectively opened and closed with respect to one side of the housing 210 and the outside under atmospheric pressure so that the new loading boat is received in the chamber and the empty loading boat is drawn from the chamber, a vacuum pump (not shown), which creates a vacuum in the chamber 271, and opening and closing devices (not shown), which selectively open and close the chamber 271 with respect to one side of the housing 210 and the outside under atmospheric pressure.

Meanwhile, in the replacement means 270, the chamber 271 may be constituted by a load lock chamber, which is typically used in LCD devices. The replacement means 270 may include a movable robot (not shown), which is provided in the load lock chamber so as to move the loading boat to the housing 210, the load lock chamber, or the outside under atmospheric pressure, thereby automatically replacing the loading boat.

Hereinafter, a method of purifying the organic material using the apparatus for purifying the organic material of the present embodiment will be described.

First, the loading boat 221, receiving the raw material of the organic material, is provided in the housing 210, and the pump 254, the circulation pump 256, and the driving motor 233 are driven to apply the ionic liquid on the surface of the blade 232 and over the entire internal surface of the housing 210. Subsequently, a vacuum is created in the housing 210 using the vacuum pump 211.

Next, the loading boat 221 is heated just before the sublimation point of the raw material of the organic material using the heater, is left for 1 to 5 min, and is further heated to the sublimation point or higher. Accordingly, the sublimated gas of the organic material is obtained. The sublimated gas includes the organic material and impurities. Meanwhile, the pump 254 and the circulation pump 256 are operated from the time at which the sublimated gas of the organic material is formed, thus spraying the ionic liquid through the communication holes 252. Further, the driving motor 233 is operated to rotate the blade 232, thereby enabling the sublimated gas to flow to the other side of the housing 210. Further, the heater 215, provided on the external surface of the housing 210, is used to increase the internal temperature of the housing 210 to the temperature at which the organic material is easily recrystallized.

The sublimated gas flows to the other side of the housing 210 to bring the surface of the blade 232 into contact with the ionic liquid and also into contact with the ionic liquid, sprayed through the communication holes 252. The sublimated gas is captured in the ionic liquid due to the contact and then gradually dissolved to be recrystallized, thus being collected in the storage tank 241 at the lower part of the housing 210. That is, when the sublimated gas is dissolved in the ionic liquid, the content of the organic material to be purified is absolutely higher than that of the impurity. Accordingly, the organic material is preferentially oversaturated to thus start recrystallization first. Thereby, the organic material is deposited at high purity.

Meanwhile, the solubility of the sublimated gas dissolved in the ionic liquid may be controlled using the heater 215 provided on the external surface of the housing 210. Therefore, the solubility of the sublimated gas to the ionic liquid may be controlled to thus control the degree of oversaturation and the recrystallization rate of the organic material in the ionic liquid. Therefore, mixing with the impurity may be minimized during the recrystallization process, and the high-purity organic material, deposited in the ionic liquid, may be appropriately collected from the storage tank 241 of the housing 210.

For example, when the recrystallized organic material is precipitated downward in the ionic liquid, the purified organic material may be collected using the collection box 261 of the collection means 260 connected to the storage tank 241. However, when the recrystallized organic material is not precipitated downward in the ionic liquid but floats on the surface of the ionic liquid or is mixed in the ionic liquid, after the mixture solution and the recrystallized organic material are discharged from the storage tank 241 to the outside of the storage tank 241, the recrystallized organic material may be separated using filtration or centrifugation to thus be collected in the collection container 255, and then the mixture solution may be recirculated into the capturing means 230 using the circulation pump 256.

In addition, when the raw material of the organic material is completely sublimated in the loading boat 221, the loading boat 221 may be replaced with a new loading boat, containing the raw material of the organic material, using the replacement means 270. The organic material may be continuously purified according to the aforementioned procedure.

After the high-purity organic material, which is deposited in the ionic liquid, is collected, the organic material, which was included in the sublimated gas, is dissolved to be oversaturated in the ionic liquid, and a small amount of the impurity remains in the ionic liquid. Further, as the purification process progresses, the content of the impurity in the ionic liquid is increased, and the impurity components are oversaturated after a predetermined amount of time. Accordingly, the impurity is mixed with the recrystallized organic material. In this case, it is preferable to replace the ionic liquid, used during the purification process, with the high-purity ionic liquid.

Third Embodiment

Figure 12:
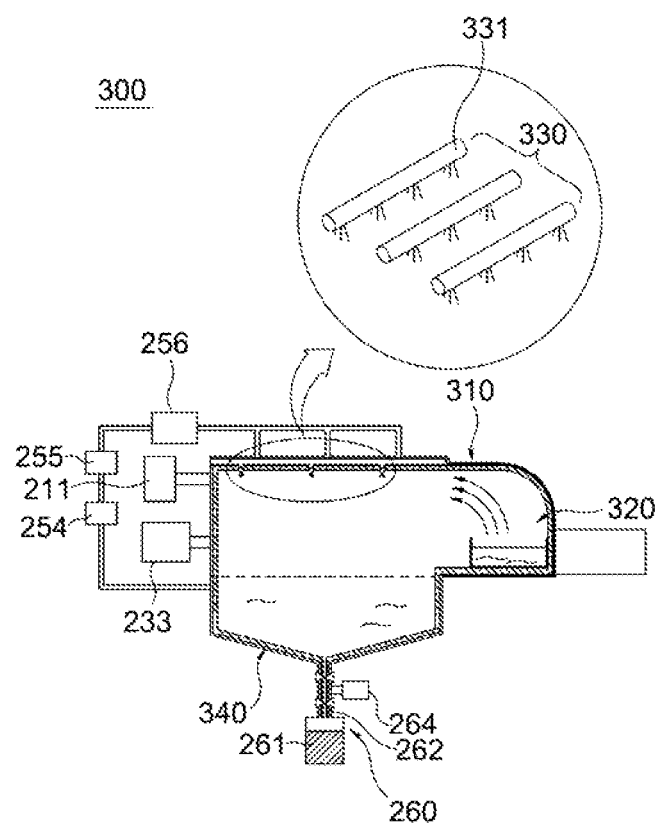
FIG. 12 is a conceptual view showing the constitution of a spray-type apparatus for purifying an organic material using an ionic liquid according to a third embodiment of the present invention.

FIG. 12 is a conceptual view showing the constitution of a spray-type apparatus for purifying an organic material using an ionic liquid according to a third embodiment of the present invention. As shown in FIG. 12, an apparatus 300 for purifying the organic material of the present embodiment includes a housing 310, which has a predetermined internal volume in a vacuum, a sublimation means 320, which is disposed at one side of the housing 310 to heat the raw material of the organic material for OLEDs, containing the impurity, to thus sublimate the raw material of the organic material, a capturing means 330, which brings the sublimated gas of the organic material into contact with the ionic liquid to capture the sublimated gas, and a recrystallization means 340 oversaturating the sublimated gas, captured in the ionic liquid by the capturing means 330 to be dissolved, thus generating the recrystallized organic material. Meanwhile, it is preferable that the apparatus 300 for purifying the organic material of the present embodiment further include a control means (not shown) controlling the operation of the sublimation means 320, the capturing means 330, and the recrystallization means 340.

In the apparatus 300 for purifying the organic material of the present embodiment, the capturing means 330 is a spray means spraying the ionic liquid while the sprayed ionic liquid forms various shapes, such as a curtain, so that the ionic liquid crosses the scattering path of the sublimated gas. That is, the spray means serves as an ionic liquid supply means, which supplies the ionic liquid so that the ionic liquid falls down to cross the scattering path of the sublimated gas. Therefore, the apparatus 300 for purifying the organic material of the present embodiment is the same as the apparatus 200 for purifying the organic material of the second embodiment, except that the capturing means 230 is omitted and the spray means 250 is partially modified. Therefore, the description of constitutional elements that are the same as those of the second embodiment will be omitted in the present embodiment.

The capturing means 330 of the present embodiment includes a plurality of spray pipes 331 having a plurality of nozzles through which the ionic liquid is sprayed. The plurality of spray pipes 331 are provided at predetermined intervals in the direction of the scattering path of the sublimated gas to spray the ionic liquid while the sprayed ionic liquid forms various shapes, such as a curtain, through the nozzles downward so that the ionic liquid comes into contact with the sublimated gas. Preferably, in the plurality of spray pipes 331, the plurality of nozzles are disposed in a zigzag arrangement so that all of the scattered sublimated gas comes into contact with the ionic liquid to thus be gradually captured.

Fourth Embodiment

Figure 13:
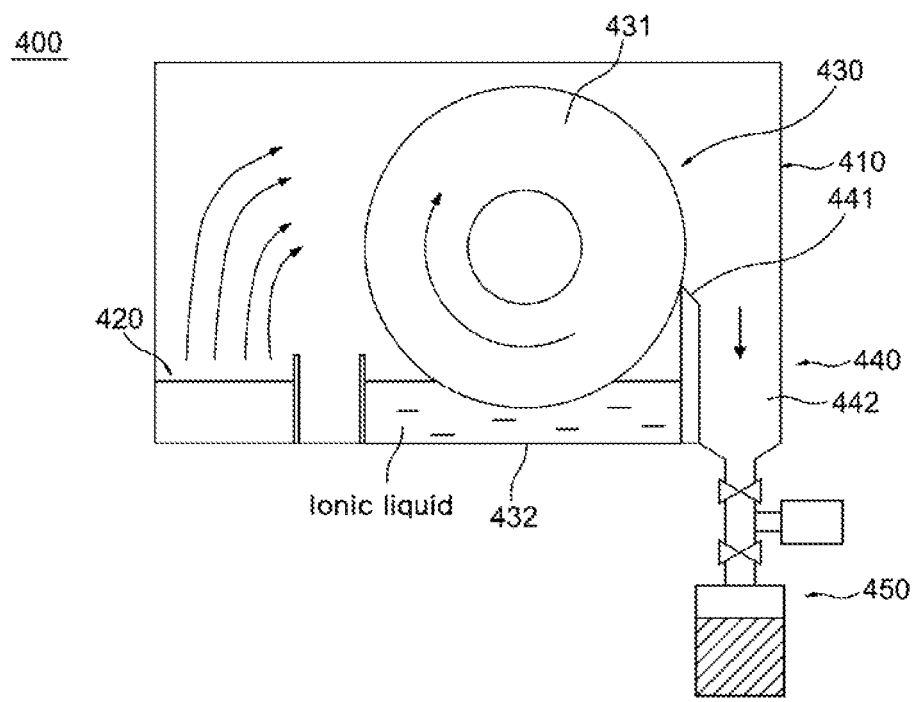
FIG. 13 is a conceptual view showing the constitution of a roll-type apparatus for purifying an organic material using an ionic liquid according to a fourth embodiment of the present invention.

FIG. 13 is a conceptual view showing the constitution of a roll-type apparatus for purifying an organic material using an ionic liquid according to a fourth embodiment of the present invention. As shown in FIG. 13, an apparatus 400 for purifying the organic material of the present embodiment includes a housing 410, which has a predetermined internal volume in a vacuum, a sublimation means 420, which is disposed at one side of the housing 410 to heat the raw material of the organic material for OLEDs, containing an impurity, to thus sublimate the raw material of the organic material, a capturing means 430, which brings the sublimated gas of the organic material into contact with the ionic liquid to capture the sublimated gas, and a recrystallization means 440, oversaturating the sublimated gas, captured in the ionic liquid by the capturing means 430 and dissolved, thus generating the recrystallized organic material.

The apparatus 400 for purifying the organic material of the present embodiment is the same as the apparatus 200 for purifying the organic material of the second embodiment, except that the capturing means 430 is provided with at least one rotating roll 431, which is disposed in the housing 410 to cross the scattering path of the sublimated gas, and that the recrystallization means 440 is provided with a doctor blade 441, which is provided at one side of the rotating roll 431 to remove the mixture solution, including the sublimated gas dissolved in the ionic liquid, from the surface of the rotating roll 431. Therefore, the description of the portion of the present embodiment that overlaps the second embodiment will be omitted.

The capturing means 430 of the present embodiment includes at least one rotating roll 431, which is disposed in the housing 410 to cross the scattering path of the sublimated gas, and an ionic liquid storage unit 432, which is disposed beneath the rotating roll 431 to supply the ionic liquid to the surface of the rotating roll 431. The rotating roll 431 rotates while the lower part of the rotating roll is dipped in the ionic liquid stored in the ionic liquid storage unit 432. Therefore, the ionic liquid is applied on the surface of the rotating roll 431, and the sublimated gas comes into contact with the surface of the applied ionic liquid to thus be captured and dissolved. Accordingly, the mixture solution, including the sublimated gas dissolved in the ionic liquid, is formed on the surface of the rotating roll 431. Meanwhile, a plurality of rotating rolls 431 may be disposed parallel to each other in the housing 410.

The recrystallization means 440 of the present embodiment includes the doctor blade 441, which is provided at one side of the rotating roll 431 to remove the mixture solution from the surface of the rotating roll 431, and a storage tank 442, in which the mixture solution is collected using the doctor blade 441 to oversaturate the organic material, thus generating the recrystallized organic material. Meanwhile, the recrystallized organic material may be collected using a separate collection means 450 connected to the storage tank 442. The collection means 450 may be the same as the collection means 260 of the second embodiment.

Hereinafter, the method of purifying the organic material using the ionic liquid according to the present invention, and the method of purifying the organic material using the apparatus for purifying the organic material, described in the aforementioned embodiments, will be described.

Figure 14:
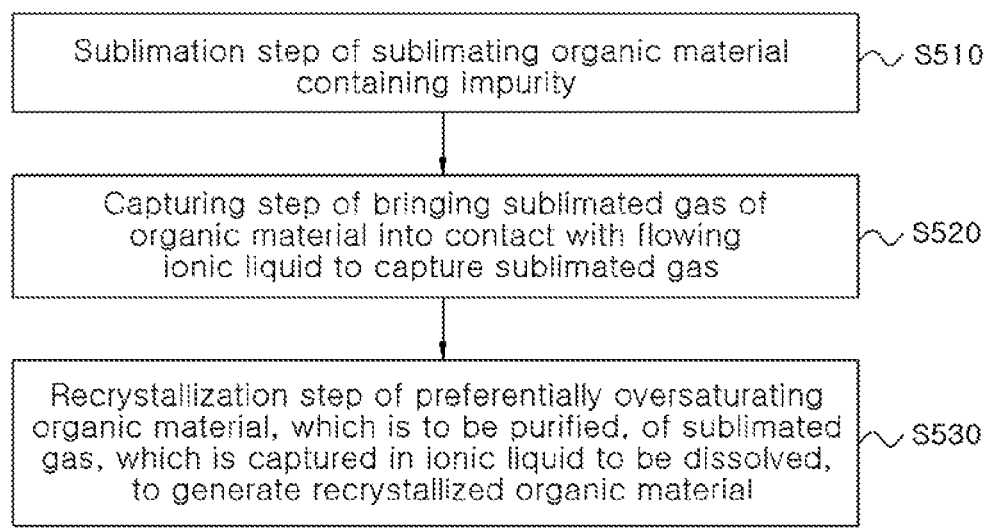
FIG. 14 is a flowchart of a method of purifying an organic material using an ionic liquid according to the present invention.

FIG. 14 is a flowchart of the method of purifying the organic material using the ionic liquid according to the present invention. As shown in FIG. 14, the method of purifying the organic material using the ionic liquid according to the present invention includes a sublimation step (S510) of sublimating the organic material for OLEDs (organic light emitting diodes), containing an impurity, a capturing step (S520) of bringing the sublimated gas of the organic material into contact with the flowing ionic liquid to capture the sublimated gas, and a recrystallization step (S530) of oversaturating the sublimated gas, which is captured in the ionic liquid to be dissolved, to thus generate the recrystallized organic material. The sublimation step (S510) includes both sublimating the organic material, which is to be purified, from a solid state to a gas state, and vaporizing the organic material from a solid state through a gel state to a gas state.

Meanwhile, as shown in FIGS. 1 to 11, the ionic liquid may flow along the surfaces of the plurality of blades 132, 132A, 132B, or 232, which are disposed to cross the scattering path of the sublimated gas, during the capturing step (S520). More specifically, as shown in FIGS. 1 to 10, the ionic liquid may flow downward along the surfaces of the plurality of blades 132, 132A, or 132B disposed at equal angles based on a vertical axis. Alternatively, the ionic liquid may flow due to the plurality of blades 232, which are disposed at equal angles based on a horizontal axis to rotate, as shown in FIG. 11, or the ionic liquid may flow and fall down to cross the scattering path of the sublimated gas, as shown in FIG. 12.

In addition, the recrystallization step (S530) may further include recirculating the mixture solution, which includes the sublimated gas dissolved in the ionic liquid, along the surfaces of the plurality of blades 132, 132A, 132B, or 232, as shown in FIGS. 1 to 11, or recirculating the mixture solution so that the mixture solution crosses the scattering path of the sublimated gas, as shown in FIG. 12. Meanwhile, the recrystallized organic material may be separated to be collected in the collection container 137 or 255, and the mixture solution may be circulated during the recirculation step.

In addition, as shown in FIG. 13, the ionic liquid may flow while being applied on the surface of at least one rotating roll 431, which is disposed to cross the scattering path of the sublimated gas, during the capturing step (S520). Meanwhile, the method may further include removing the mixture solution, which includes the sublimated gas dissolved in the ionic liquid and which is applied on the surface of the rotating roll 431, from the surface of the rotating roll 431 using the doctor blade 441, positioned at one side of the rotating roll 431, thereby collecting the mixture solution in the storage tank 442.

Hereinafter, the mechanism whereby the organic material is continuously crystallized to be purified according to the present invention will be described.

The sublimated gas of the organic material is captured in the ionic liquid and then dissolved to form the mixture solution, and the sublimated gas reaches a saturation state to form a saturated solution. After the saturated solution is formed, the sublimated gas is captured and dissolved in the saturated solution to form a nucleus, and organic material molecules are scattered around the nucleus in the saturated solution to adhere to the nucleus, thus inducing crystals to grow. The concentration of the organic material molecules is lower around the growing crystals than in the remaining area. That is, the relative concentration of the molecules around the crystals is decreased as the crystals of the molecules grow in the saturated solution. Accordingly, the saturated solution becomes the mixture solution that comes into contact with the sublimated gas to dissolve the sublimated gas therein.

Meanwhile, in the present invention, the driving force of crystal growth is attributable to the maintenance of a concentration gradient. In order to maintain the concentration gradient, two processes may be used in the present invention.

The first process is to circulate the ionic liquid. That is, the ionic liquid in a mixture solution state (not in a saturated solution state) is circulated to induce the crystals to continuously grow while the mixture solution state, the saturated solution state, and the oversaturated solution state exist together in the ionic liquid. This process may be applied when the growing speed of the nucleus is greater than the speed at which the sublimated gas is supplied.

The second process is to supply a fresh ionic liquid. That is, the fresh ionic liquid is continuously supplied to induce the crystals to continuously grow while the mixture solution state, the saturated solution state, and the oversaturated solution state exist together in the ionic liquid. This process may be applied when the growing speed of the nucleus is smaller than the supply speed of the sublimated gas. That is, this process prevents the direct crystallization of the sublimated gas into solids without the dissolution of the sublimated gas in the ionic liquid due to the increased degree of oversaturation.

Hereinafter, whether or not the organic material is purified using the apparatus and the method for purifying the organic material using the ionic liquid according to the present invention, and the properties of the purified organic material will be described.

1. Apparatus and Method for Purifying Organic Material

Figure 15:
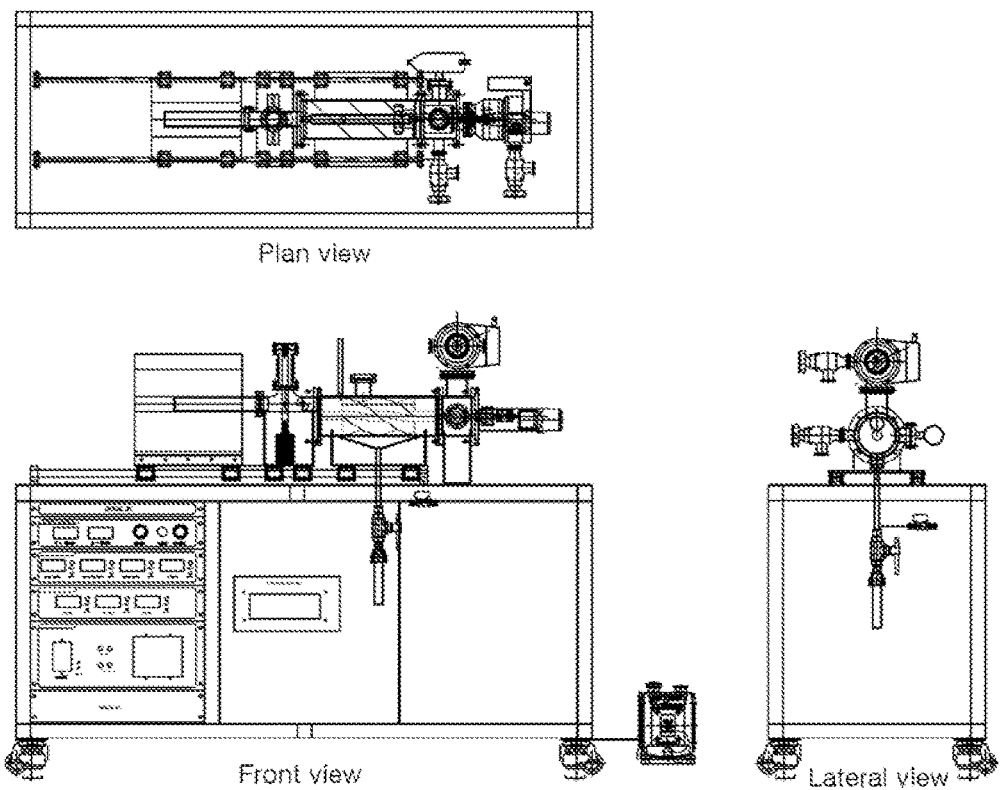
FIG. 15 is a design view showing the manufacture of the horizontal-type apparatus for purifying the organic material.

FIG. 15 is a design view showing the manufacture of the horizontal-type apparatus for purifying the organic material. As shown in FIG. 15, the horizontal-type apparatus for purifying the organic material includes a sublimation unit, which sublimates the organic material for OLEDs containing the impurity, and a capturing unit, which communicates with the sublimation unit to bring the sublimated gas of the organic material into contact with the flowing ionic liquid, thus capturing the sublimated gas. The sublimation unit is the same as the sublimation unit shown in FIG. 11. The capturing unit is the same as the capturing unit shown in FIG. 11, and the blade rotates based on a horizontal axis in the housing (chamber) to bring the sublimated gas into contact with the ionic liquid to thus capture and dissolve the sublimated gas, thereby recrystallizing the organic material.

The procedure of the purification experiment using the horizontal-type apparatus for purifying the organic material is as follows. First, the organic material, which is to be purified, is charged in the sublimation unit under atmospheric pressure, the ionic liquid is injected into the capturing unit, and the chamber undergoes pumping under $1 \times 10^{-6}$ Torr. Subsequently, the ionic liquid is heated, the blade of the capturing unit rotates, and the organic material, which is to be purified, is heated to the sublimation point and then maintained at the sublimation point for a predetermined time so that the organic material to be purified is sublimated. The sublimated gas of the organic material is then scattered and comes into contact with the ionic liquid, flowing along the blade, to be captured and dissolved, thereby being recrystallized. After the purification process is finished, the purified organic material is collected and separated from the ionic liquid, and the ionic liquid remaining on the surface of the purified organic material is washed.

2. Experimental Condition and Result of Apparatus for Purifying Organic Material 1 kg of OMIM TFSI (1-octyl-3-methylimidazolium bis (trifluoromethyl sulfonyl)imide) was used as the ionic liquid, and 20 g of the HTL material (DS 220) was used as the organic material. Meanwhile, the sublimation temperature of the organic material was set to 280° C. or higher and the temperature of the ionic liquid was set to 120° C. during a purification experiment. In addition, sublimation was initiated after pressure was reduced to $1 \times 10^{-6}$ Torr, and a processing time was 5 hours.

During the purification experiment under the aforementioned conditions, organic material crystals were observed to float on the surface of the ionic liquid 30 min after sublimation was initiated, and it was observed that the amount of the crystals increased over time. That is, it was confirmed that the organic material purified using recrystallization was present in the form of floating matter on the surface of the ionic liquid. This means that the organic material can be purified using the ionic liquid.

After the purification process is finished, the mixture of the purified organic material and the ionic liquid was collected, and the purified organic material was separated from the ionic liquid, followed by washing. Various kinds of analysis were then performed.

3. Analysis of Properties of Purified Organic Material

The properties of the purified organic material were analyzed using the analysis instruments of Table 1 under the following conditions.

TABLE 1

| Analysis instrument | Apparatus model | Manufacturer | Measurement condition |
|---|---|---|---|
| FE-SEM | Quanta 200 | PEI Company | HV: 20 kV<br>Spot size: 3 mm<br>Magnification: 1k-30k |
| Raman | LabRamHR | JOVIN YVON | 514 nm Ar laser<br>Temperature: 21° C.<br>Humidity: 20%<br>Scan range: 1000-3000 $cm^{-1}$ |
| PL | RPM2000 | ACCENT | 325 nm He—Cd Laser<br>Temperature: 21° C.<br>Humidity: 20%<br>Scan range: 350-810 nm |
| XPS | VG Multilab 2000 | ThermoVG Scientific | Lens mode: LAXPS<br>Survey pass energy: 50 eV<br>Narrow pass energy: 20 eV<br>Analysis elements: C, O, F, Cl, S |

4. Raman PL Measurement

Figure 16:
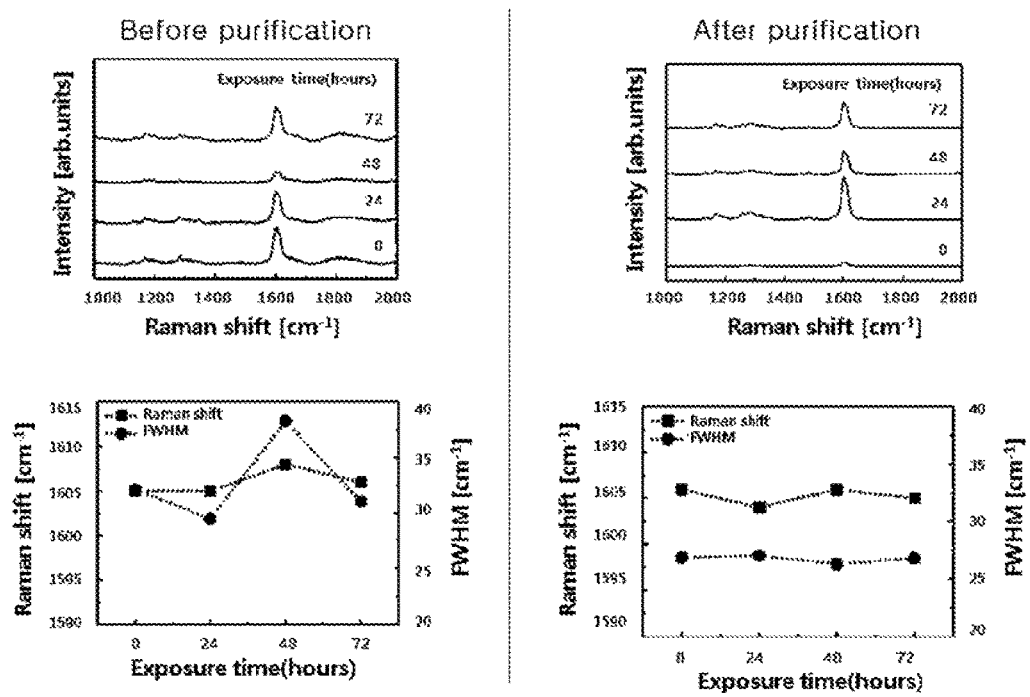
FIG. 16 is a graph showing a change in a Raman PL property, obtained by measuring the Raman PL property of a HTL material, depending on an air-exposure time, before and after purification using the horizontal-type apparatus for purifying the organic material shown in FIG. 15.

A change in the Raman PL property of a HTL material depending on an air-exposure time was measured before and after purification. The Raman PL measurement was performed to compare the stabilities of the organic material of the HTL material, depending on the air-exposure time, before and after purification. FIG. 16 is a graph showing a change in a Raman PL property obtained by measuring the Raman PL property of the HTL material, depending on the air-exposure time, before and after purification using the horizontal-type apparatus for purifying the organic material shown in FIG. 15.

From FIG. 16, it was confirmed that a change in half width (FWHM) of the peak of the HTL material before purification was 8 $cm^{-1}$ as the air-exposure time was increased but, after purification, that of the HTL material was 0.5 $cm^{-1}$ and the HTL material was very stable. This means that the surface of the organic material purified using the ionic liquid is passivated by the ionic liquid component.

5. PL Measurement

Figure 17:
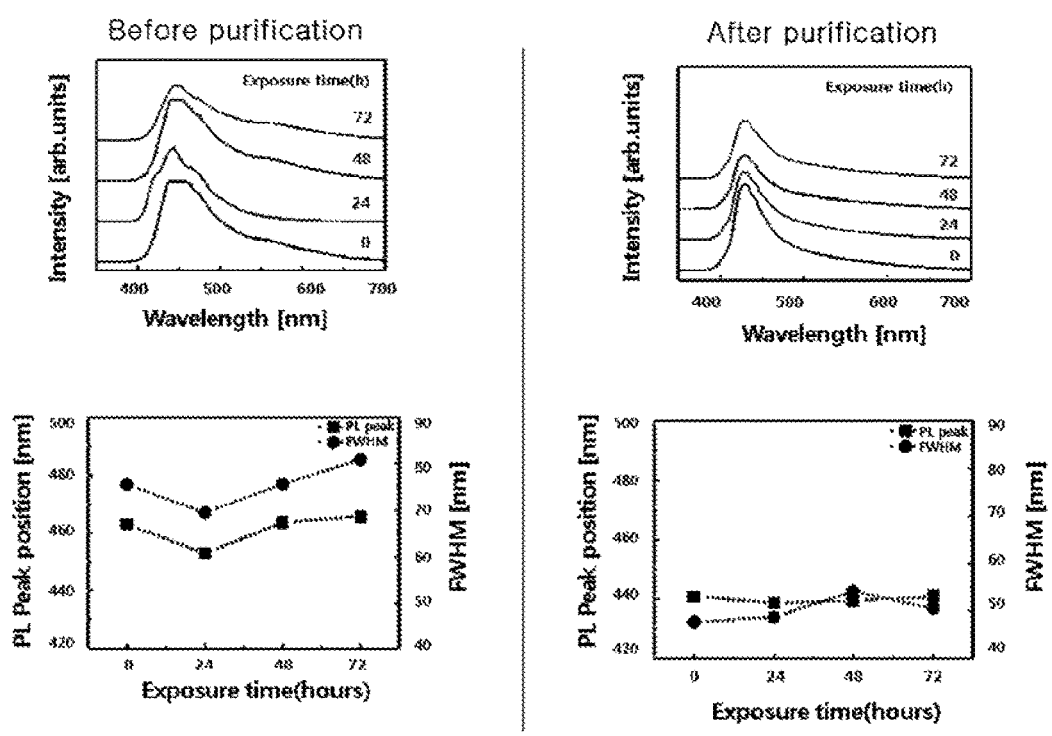
FIG. 17 is a graph showing a change in a PL property, obtained by measuring the PL property of a HTL material, depending on an air-exposure time, before and after purification using the horizontal-type apparatus for purifying the organic material shown in FIG. 15.

A change in a PL property of a HTL material, depending on an air-exposure time, before and after purification was measured. The PL measurement was performed to compare the stabilities of the organic material of the HTL material, depending on the air-exposure time, before and after purification. FIG. 17 is a graph showing changes in a PL property obtained by measuring the PL property of the HTL material, depending on the air-exposure time, before and after purification using the horizontal-type apparatus for purifying the organic material shown in FIG. 15.

From FIG. 17, it can be seen that, after purification, the position of the emission peak of the HTL material is shifted to a short wavelength (460 nm→440 nm) and the value of a half width (FWHM) is reduced from 75 nm to 50 nm. This means that the purity of the material is improved due to the purification process. Further, it can be seen that, before purification, a change in a peak position of the HTL material is ±5 nm and a change in a half width (FWHM) is 10 nm as the air-exposure time is increased but, after purification, a change in a peak position of the HTL material is ±1 nm or less and a change in a half width (FWHM) is 5 nm or less. Accordingly, changes in the properties of the organic material, purified using the ionic liquid, due to external moisture and oxygen were insignificant. This means that the surface of the organic material purified using the ionic liquid is passivated by the ionic liquid component.

6. SEM Measurement

Figure 18:
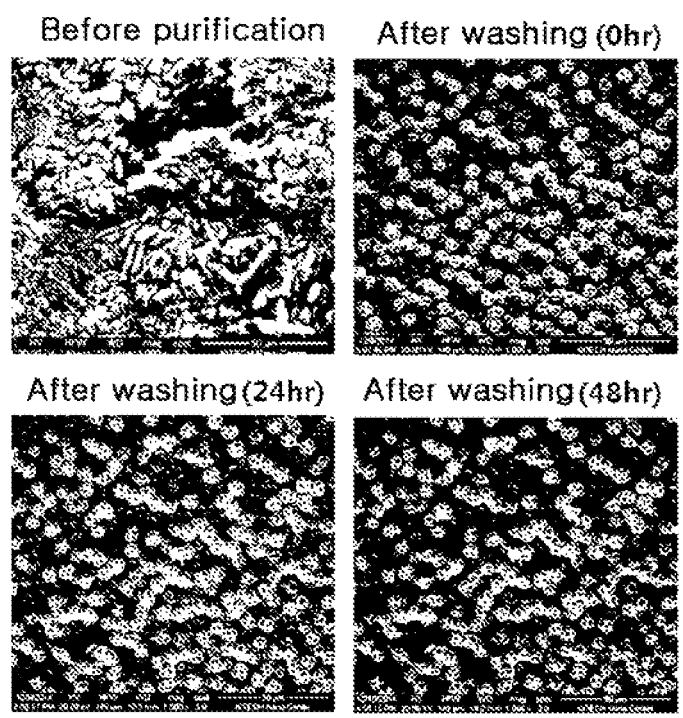
FIG. 18 is a SEM (×1 k) picture showing a change in surface shape, obtained by photographing the surface shape of a HTL material, depending on an air-exposure time, before and after purification using the horizontal-type apparatus for purifying the organic material shown in FIG. 15.

A change in surface shape of a HTL material, depending on an air-exposure time, before and after purification was measured. The PL measurement was performed to compare the stabilities of the organic material of the HTL material, depending on the air-exposure time, before and after purification. FIG. 18 is a SEM (×1 k) picture showing a change in surface shape obtained by photographing the surface shape of the HTL material, depending on the air-exposure time, before and after purification using the horizontal-type apparatus for purifying the organic material shown in FIG. 15.

The HTL material is a material that is obtained immediately after synthesis and has a purity of about 98.6% before purification. As seen from FIG. 18, nothing unusual was observed in terms of the surface shape in the HTL material before purification. However, spherical crystal particles were observed in the HTL material purified using the horizontal-type apparatus for purifying the organic material according to the present invention. The crystal particles were 5 μm in size and the sizes thereof were very uniform. Meanwhile, a significant change in surface shape was not observed over time.

7. XPS Measurement

Figure 19:
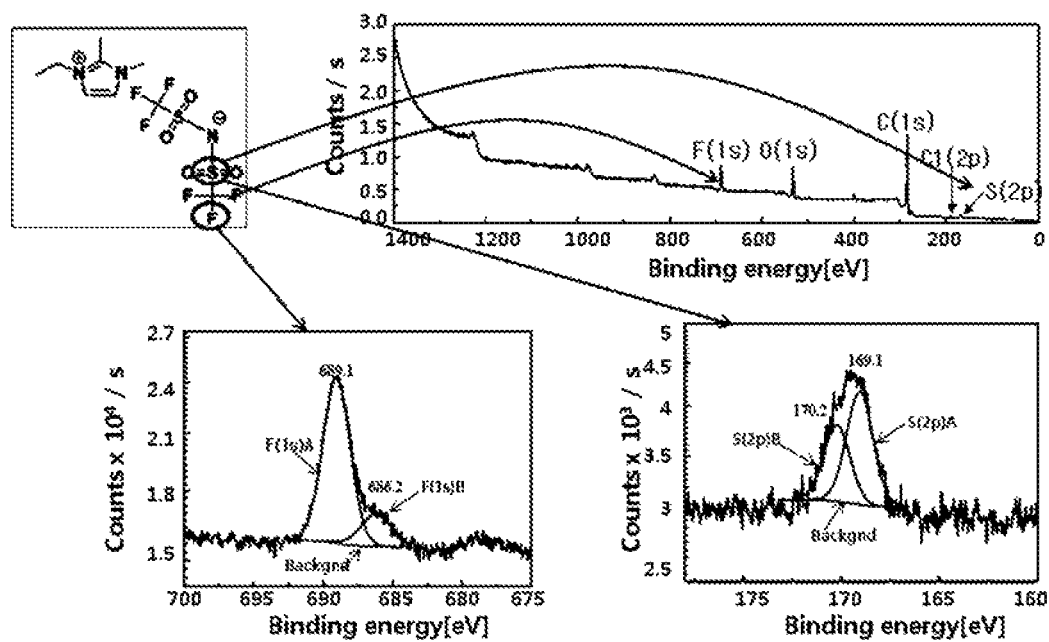
FIG. 19 is an XPS graph showing the properties of the organic material purified using the horizontal-type apparatus for purifying the organic material shown in FIG. 15.

The properties of the organic material purified using the horizontal-type apparatus for purifying the organic material according to the present invention were checked by performing the XPS measurement. FIG. 19 is an XPS graph showing the properties of the organic material purified using the horizontal-type apparatus for purifying the organic material shown in FIG. 15.

As seen from FIG. 19, F and S elements were detected, and the F and S elements were attributable to anion components of the ionic liquid used to purify the organic material. This is the intrinsic result of the method of purifying the organic material using the ionic liquid, and shows that anions and cations are chemically bonded at the level of molecules on the surface of the recrystallized organic material during the purification process. Therefore, it can be seen that the surface of the purified organic material is passivated by the ionic liquid, the components from the ionic liquid (the components constituting the ionic liquid), or the ions constituting the ionic liquid. Particularly, it can be seen that the surface of the purified organic material is passivated by the anions of the single molecular layer chemically bonded thereto. In conclusion, it can be seen that since the surface of the purified organic material is passivated, the properties of the purified organic material are stably maintained when the organic material is exposed to the atmosphere. The aforementioned characteristic, that is, the detection of infinitesimal amounts of the special component elements from the ionic liquid that was used, is the intrinsic characteristic of the organic material purified according to the purification method using the ionic liquid. Whether or not the target organic material is a material purified according to the purification method using the ionic liquid can be confirmed by checking the aforementioned characteristic. Therefore, the present invention provides an organic material exhibiting the aforementioned purified material characteristic.

However, when the F and S components from the ionic liquid are mixed during a device process, the F and S components may negatively affect the properties of the device during a process of manufacturing an OLED panel. Therefore, the F and S components from the ionic liquid, passivating the surface of the purified organic material, should be removed immediately before a deposition process performed to manufacture the device.

Accordingly, the present inventor has conducted experiments, and confirmed that the components from the ionic liquid, passivating the surface of the organic material, were completely removed using Ar ion etching or heat treatment at 100° C. or higher. If the impurities are present in the organic material, the impurities cannot be removed using the method such as the heat treatment or simple Ar ion etching. Accordingly, the aforementioned result proves that the components from the ionic liquid are present in an infinitesimal amount only on the surface of the purified organic material.

Figure 20:
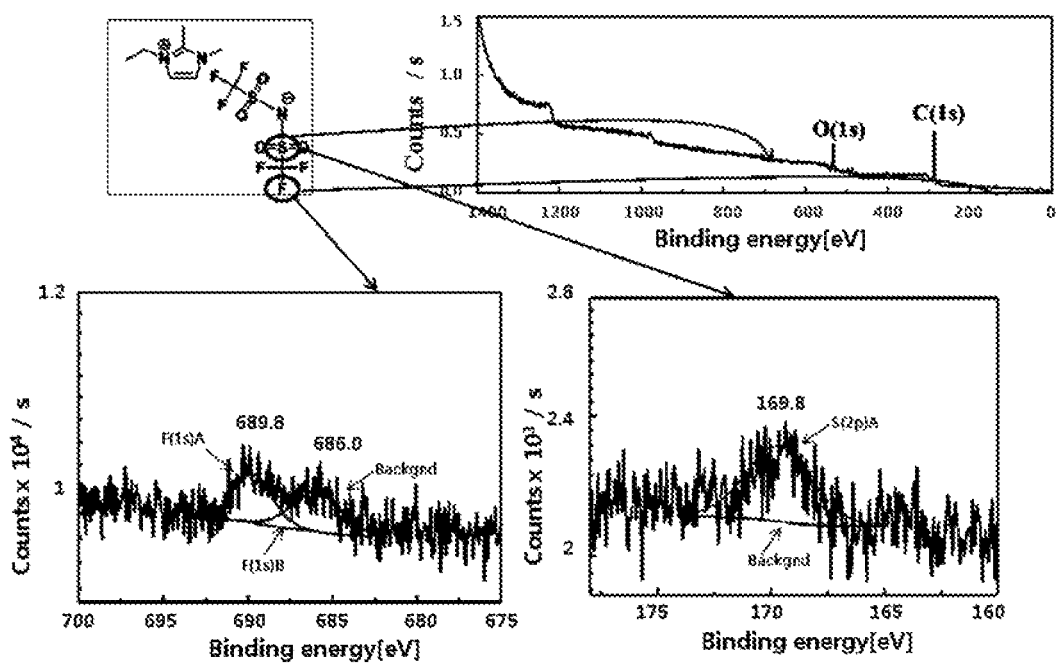
FIG. 20 is a graph obtained by analyzing the surface composition of the organic material using an XPS after the purified organic material is heat-treated at 120° C. for 1 min.

FIG. 20 is a graph obtained by analyzing the surface composition of the organic material using an XPS after the purified organic material is heat-treated at 120° C. for 1 min. As seen from FIG. 20, very weak peaks were detected at the positions of the F and S components. This means that most of the F and S components present on the surface of the purified organic material was removed using heat treatment. Accordingly, it is confirmed that the purified organic material can be stably handled during a distribution process until the purified organic material is added to a device process. Further, it is confirmed that the components from the ionic liquid, passivating the surface of the organic material, can be completely removed using appropriate pre-treatment immediately before the device process to thus prevent adverse effects on the device process.

Although technical matters of a method and an apparatus for purifying an organic material using an ionic liquid according to the present invention are described along with the accompanying drawings, these are illustrative of the most preferred embodiment of the present invention. Therefore, the present invent ion is not limited to the aforementioned embodiments, but those skilled in the art will appreciate that various modifications and changes are possible, without departing from the spirit and scope of the invention, and accordingly, such changes or modifications fall under the claims of the present invention.

INDUSTRIAL APPLICABILITY

Examples of an organic material include an organic TFT material, an organic solar battery material, and an organic semiconductor material, in addition to a low-molecular weight organic light-emitting material for use in the manufacture of an OLED device. Therefore, the present invention may be used to purify the organic material applied to the various aforementioned fields.

The invention claimed is:

1. A method of purifying an organic material using an ionic liquid, the method comprising:
a sublimation step of sublimating a raw organic material containing an impurity,
a capturing step of capturing a sublimated gas of the raw organic material in the ionic liquid by bringing the sublimated gas into contact with the ionic liquid flowing across the sublimated gas, and
a recrystallization step of generating a recrystallized organic material from a solution supersaturated with the organic material of the sublimated gas dissolved in the ionic liquid.

2. The method of claim 1, wherein the ionic liquid flows along surfaces of a plurality of blades, which are disposed to cross a scattering path of the sublimated gas, during the capturing step.

3. The method of claim 2, wherein the recrystallization step further includes a recirculation step of recirculating a mixture solution including the sublimated gas dissolved in the ionic liquid along the surfaces of the plurality of blades.

4. The method of claim 2, wherein the plurality of blades are disposed at equal angles based on a vertical axis so that the ionic liquid flows downward along the surfaces of the plurality of blades.

5. The method of claim 2, wherein the plurality of blades are disposed at equal angles based on a horizontal axis and rotate to enable the ionic liquid to flow.

6. The method of claim 1, wherein the ionic liquid flows and falls down to cross a scattering path of the sublimated gas during the capturing step.

7. The method of claim 6, wherein a recrystallization step further includes a recirculation step of recirculating a mixture solution including the sublimated gas dissolved in the ionic liquid to cross the scattering path of the sublimated gas.

8. The method of claim 7, wherein a recrystallized organic material is separated to be collected and the mixture solution is circulated during the recirculation step.

9. The method of claim 1, wherein the ionic liquid flows to be applied on a surface of at least one rotating roll, which is disposed to cross a scattering path of the sublimated gas, during the capturing step.

10. The method of claim 9, further comprising:
removing a mixture solution, which includes the sublimated gas dissolved in the ionic liquid, from the surface of the rotating roll using a doctor blade.

11. An apparatus for purifying an organic material using an ionic liquid, the apparatus comprising:
a sublimation unit for sublimating a raw organic material containing an impurity, and
a capturing unit disposed to communicate with the sublimation unit for capturing a sublimated gas of the raw organic material in the ionic liquid by bringing the sublimated gas into contact with the ionic liquid flowing across the sublimated gas,
wherein the organic material of the sublimated gas captured in the ionic liquid is dissolved in the ionic liquid, to thus generate a recrystallized organic material in the ionic liquid.

12. The apparatus of claim 11, wherein the capturing unit includes
a housing communicating with the sublimation unit,
a plurality of blades disposed in the housing to cross a scattering path of the sublimated gas,
an ionic liquid supply means supplying the ionic liquid so as to enable the ionic liquid to flow along surfaces of the plurality of blades, and
a storage means storing a mixture solution, which includes the sublimated gas dissolved in the ionic liquid, and the recrystallized organic material.

13. The apparatus of claim 12, wherein the ionic liquid supply means further includes a recirculation means recirculating the mixture solution from the storage means along the surfaces of the plurality of blades.

14. The apparatus of claim 13, wherein the plurality of blades are disposed at equal angles based on a vertical axis in a housing.

15. The apparatus of claim 13, wherein the plurality of blades are disposed at equal angles based on a horizontal axis in a housing to rotate.

16. The apparatus of claim 11, wherein the capturing unit includes
a housing communicating with the sublimation unit,
an ionic liquid supply means supplying the ionic liquid so that the ionic liquid falls down to cross a scattering path of the sublimated gas, and a storage means storing a mixture solution, which includes the sublimated gas dissolved in the ionic liquid, and the recrystallized organic material.

17. The apparatus of claim 16, wherein the ionic liquid supply means further includes a recirculation means recirculating the mixture solution from the storage means so that the mixture solution falls down to cross the scattering path of the sublimated gas.

18. The apparatus of claim 17, wherein the recirculation means further includes a collection means, which discharges the mixture solution and a recrystallized organic material from the storage means to an outside, separates the recrystallized organic material to collect the recrystallized organic material, and recirculates the mixture solution.

19. The apparatus of claim 11, wherein the capturing unit includes
a housing communicating with the sublimation unit,
at least one rotating roll disposed in the housing to cross a scattering path of the sublimated gas, and
an ionic liquid storage unit disposed beneath the rotating roll to supply the ionic liquid to a surface of the rotating roll.

20. The apparatus of claim 19, wherein a doctor blade is provided at one side of the rotating roll to remove a mixture solution including the sublimated gas dissolved in the ionic liquid from the surface of the rotating roll.

* * * * *